United States Patent
Jolidon et al.

(10) Patent No.: US 7,235,581 B2
(45) Date of Patent: *Jun. 26, 2007

(54) 4-PYRROLIDINO-PHENYL-BENZYL ETHER DERIVATIVES

(75) Inventors: Synese Jolidon, Blauen (CH); Rosa Maria Rodriguez-Sarmiento, Basel (CH); Andrew William Thomas, Birsfelden (CH); Wolfgang Wostl, Grenzach-Wyhlen (DE); Rene Wyler, Zurich (CH)

(73) Assignee: Hoffman-La Roche Inc., Nutley, NJ (US)

( * ) Notice: Subject to any disclaimer, the term of this patent is extended or adjusted under 35 U.S.C. 154(b) by 407 days.

This patent is subject to a terminal disclaimer.

(21) Appl. No.: 10/666,594

(22) Filed: Sep. 18, 2003

(65) Prior Publication Data

US 2004/0097578 A1  May 20, 2004

(30) Foreign Application Priority Data

Sep. 20, 2002  (EP) .................................. 02021319

(51) Int. Cl.
*A61K 31/4015* (2006.01)
*C07D 207/04* (2006.01)

(52) U.S. Cl. ...................... 514/424; 548/541; 548/543; 548/550; 548/551

(58) Field of Classification Search ................ 548/541, 548/543, 551, 550; 514/424
See application file for complete search history.

(56) References Cited

U.S. PATENT DOCUMENTS 4,287,351 A  9/1981 Bourgery et al.
6,495,548 B1 * 12/2002 Duan ...................... 514/231.5

FOREIGN PATENT DOCUMENTS

| EP | 0393607 | 10/1990 |
|---|---|---|
| EP | 0 985 665 | 3/2000 |
| FR | 2 500 831 | 9/1982 |
| WO | WO 96/40095 | 12/1996 |
| WO | WO 97/33572 | 9/1997 |
| WO | WO 01/34172 | 5/2001 |

OTHER PUBLICATIONS

Bach, A. W. J., et al. Proc. Natl. Acad. Sci. USA 85:4934-4938 (1988).
Cesura, A. M., & Pletscher, A., Prog. Drug Research 38:171-297 (1992).
Fowler, C. J., et al. J. Neural. Transm. 49:1-20 (1980).
Benedetti, M. S., et al. Biochem. Pharmacol. 38:555-561 (1989).
Saura, J., et al. Neuroscience 70:755-774 (1996).
Bentué-Ferrer, D., et al. CNS Drugs 6(3): 217-236 (1996).
Gardner, D. M., et al. J. Clin. Psychiatry 57(3):99-104 (1996).
Ikuta, H., et al. J. Med. Chem. 30:1995-1998 (1987).
Danishefsky, S., et al. J. Amer. Chem. Soc. 97:3239-3241 (1975).
Lam, P. Y. S., et al. Tetrahedron Lett. 43:3091-3094 (2002).
Lam, P. Y. S., et al. Synlett 5:674-676 (2000).
Chan, D. M. T., et al. Tetrahedron Lett. 39:2933-2936 (1998).
Wolfe, J. P., et al. J. Amer. Chem. Soc. 118:7215-7216 (1996).
Freidinger, R. M., et al. J. Org. Chem. 47:104-109 (1982).
Schlaeger, E. J., & Christensen, K., Cytotechnology 30:71-83 (1999).
Zhou, M., & Panchuk-Voloshina, N., Analytical Biochemistry 253:169-174 (1997).
Abstract Corresponding to EP 0 985 665.

* cited by examiner

*Primary Examiner*—Golam M. M. Shameem
(74) *Attorney, Agent, or Firm*—George W. Johnston; Patricia S. Rocha-Tramaloni; Kimberly J. Prior

(57) ABSTRACT

The invention relates to racemic or enantiomerically pure 4-pyrrolidino derivatives, processes for their preparation, pharmaceutical compositions comprising said derivatives, and their use in the prevention and treatment of illness, e.g. which are mediated by monoamine oxidase B inhibitors, in particular Alzheimer's disease or senile dementia.

73 Claims, No Drawings

4-PYRROLIDINO-PHENYL-BENZYL ETHER DERIVATIVES

FIELD OF THE INVENTION

The present invention relates to new 4-pyrrolidino derivatives, to processes and intermediates for their preparation, and to pharmaceutical compositions containing them. These compounds are selective monoamine oxidase B inhibitors and, therefore, are useful for treating or preventing diseases mediated by monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethylamine, as well as a number of amine xenobiotics. The enzyme exists in two forms, MAO-A and MAO-B, encoded by different genes [Bach et al., Proc. Natl. Acad. Sci. USA 85:4934–4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171–297 (1992)]. Brain MAO-B activity appears to increase with age. This increase has been attributed to the gliosis associated with aging [Fowler et al., J. Neural. Transm. 49:1–20 (1980)]. Additionally, MAO-B activity is significantly higher in the brains of patients with Alzheimer's disease [Dostert et al., Biochem. Pharmacol. 38:555–561 (1989)] and it has been found to be highly expressed in astrocytes around senile plaques [Saura et al., Neuroscience 70:755–774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B.

Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentué-Ferrer et al. [CNS Drugs 6:217–236 (1996)]. Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99–104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The invention relates to racemic or enantiomerically pure 4-pyrrolidino derivatives, processes for their preparation, pharmaceutical compositions comprising said derivatives, and their use in the prevention and treatment of illness. More particularly, the present invention relates to compounds of the formula I

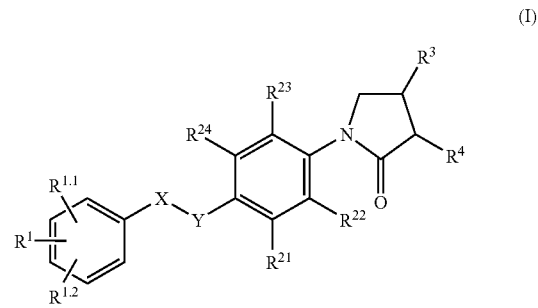

(I)

wherein
X—Y is —$CH_2$—$CH_2$—, —CH=CH— or —$CH_2$—O— and $R^1$, $R^{1.1}$, $R^{1.2}$, $R^3$, $R^4$, $R^5$, $R^6$, $R^{21}$, $R^{22}$, $R^{23}$, $R^{24}$ are as defined herein. The invention comprises individual isomers of the compounds herein as well as racemic and non-racemic mixtures thereof.

It has been found that the compounds of the invention, for example, compounds of general formula I and I* as well as individual isomers, racemic or non-racemic mixtures thereof (hereinafter: Active Compounds) are selective monoamine oxidase B inhibitors. Therefore, the invention also relates to pharmaceutical compositions and methods for treating diseases mediated by MAO-B inhibitors, for example, Alzheimer's disease and senile dementia.

The invention also relates to methods for making the compounds of the invention, for example compounds of formula I and I*.

DETAILED DESCRIPTION OF THE INVENTION

The following definitions of general terms used herein apply irrespective of whether the terms in question appear alone or in combination. It must be noted that, as used in the specification and the appended claims, the singular forms "a," "an," and "the" include plural forms unless the context clearly dictates otherwise.

The term "individual isomers, racemic or non-racemic mixtures thereof" denotes E- and Z-isomers, mixtures thereof as well as individual configurational isomers and mixtures thereof.

The term "($C_1$–$C_6$)-alkyl" used in the present application denotes straight-chain or branched saturated hydrocarbon residues with 1 to 6 carbon atoms, such as methyl, ethyl, n-propyl, i-propyl, n-butyl, sec-butyl, t-butyl, and the like, preferably with 1 to 3 carbon atoms. Accordingly, the term "($C_1$–$C_3$)-alkyl" means a straight-chain or branched saturated hydrocarbon residue with 1 to 3 carbon atoms.

"(C$_1$–C$_6$)-Alkoxy" means the residue —O—R, wherein R is a lower alkyl residue as defined herein. Examples of alkoxy radicals include, but are not limited to, methoxy, ethoxy, isopropoxy, and the like.

The term "halogen" denotes fluorine, chlorine, bromine and iodine.

"Halogen-(C$_1$–C$_6$)-alkyl" or "halogen-(C$_1$–C$_6$)-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 3,3,3-trifluoropropyl, and the like. "Halogenalkoxy" includes trifluoromethyloxy.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid. If possible, compounds of formula I may be converted into pharmaceutically acceptable salts. It should be understood that pharmaceutically acceptable salts are included in the present invention.

It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

The invention relates to racemic or enantiomerically pure 4-pyrrolidino derivatives, processes for their preparation, pharmaceutical compositions comprising said derivatives, and their use in the prevention and treatment of illness.

More particularly, the present invention relates to compounds of the formula I

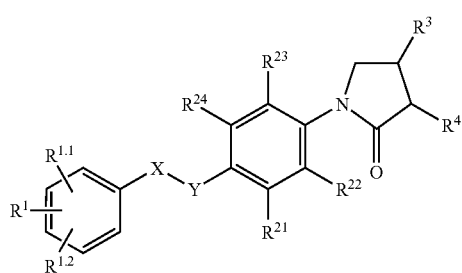

(I)

wherein

X—Y is —CH$_2$—CH$_2$—, —CH=CH— or —CH$_2$—O—;

R$^1$, R$^{1.1}$ and R$^{1.2}$ independently from each other are selected from the group consisting of hydrogen, halogen, cyano, (C$_1$–C$_6$)-alkyl, halogen-(C$_1$–C$_6$)-alkyl, (C$_1$–C$_6$)-alkoxy or halogen-(C$_1$–C$_6$)-alkoxy;

R$^{21}$, R$^{22}$ and R$^{23}$ independently from each other are selected from the group consisting of hydrogen and halogen;

R$^{24}$ is hydrogen, halogen or methyl;

R$^3$ is hydrogen;

R$^4$ is —CONHR$^5$, —CN or —NHR$^6$;

R$^5$ is hydrogen or (C$_1$–C$_3$)-alkyl; and

R$^6$ is —C(O)H, —C(O)—(C$_1$–C$_6$)-alkyl, —C(O)-halogen-(C$_1$–C$_3$)-alkyl, —C(O)O—(C$_1$–C$_3$)alkyl, —C(O)—NH$_2$ or —SO$_2$—(C$_1$–C$_6$)-alkyl;

or individual isomers, racemic or non-racemic mixtures thereof.

Even more particularly, the present invention relates to compounds of the formula I*

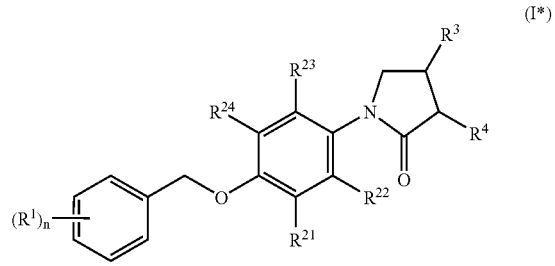

(I*)

wherein

R$^1$ is halogen, halogen-(C$_1$–C$_6$)-alkyl, cyano, (C$_1$–C$_6$)-alkoxy or halogen-(C$_1$–C$_6$)-alkoxy;

R$^{21}$, R$^{22}$, R$^{23}$ and R$^{24}$ independently from each other are selected from the group consisting of hydrogen and halogen;

R$^3$ is hydrogen;

R$^4$ is —CONHR$^5$, —CH$_2$CN, —CN or —NHR$^6$;

R$^5$ is hydrogen or C$_1$–C$_3$-alkyl;

R$^6$ is —CO—(C$_1$–C$_6$)-alkyl or —SO$_2$—(C$_1$–C$_6$)-alkyl; and n is 0, 1, 2 or 3;

or individual isomers, racemic or non-racemic mixtures thereof.

In one embodiment the present invention provides compounds of formula I*, wherein R$^3$ is hydrogen and R$^4$ is selected from the group consisting of —CONHR$^5$, —CH$_2$CN, or —CN.

Those compounds of formula I*, wherein R$^4$ is —CONHR$^5$ and R$^5$ is hydrogen or (C$_1$–C$_3$)-alkyl, are especially preferred. Examples of such compounds are (RS)-1-[4-(3-fluoro-benzyloxy)-phenyl]-2-oxo-pyrrolidine-3-carboxylic acid methylamide;

(RS)-1-[4-(3-fluoro-benzyloxy)-phenyl]-2-oxo-pyrrolidine-3-carboxylic acid amide;

(RS)-1-[4-(4-fluoro-benzyloxy)-phenyl]-2-oxo-pyrrolidine-3-carboxylic acid amide;

(RS)-1-[4-(4-fluoro-benzyloxy)-phenyl]-2-oxo-pyrrolidine-3-carboxylic acid amide;

(RS)-2-oxo-1-[4-(4-trifluoromethyl-benzyloxy)-phenyl]-pyrrolidine-3-carboxylic acid amide; and (RS)-2-oxo-1-[4-(4-trifluoromethyl-benzyloxy)-phenyl]-pyrrolidine-3-carboxylic acid methylamide.

Another group of preferred compounds of formula I* are those, wherein R$^4$ is —CN. (RS)-1-(4-benzyloxy-phenyl)-2-oxo-pyrrolidine-3-carbonitrile is an example of such a compound.

Also preferred are compounds of formula I*, wherein R$^3$ is hydrogen, R$^4$ is —NHR$^6$ and R$^6$ is —CO—(C$_1$–C$_6$)-alkyl or —SO$_2$—(C$_1$–C$_6$)-alkyl. Examples of such compounds are (S)—N-[1-(4-benzyloxy-phenyl)-2-oxo-pyrrolidin-3-yl]-acetamide and (S)—N-[1-(4-benzyloxy-phenyl)-2-oxo-pyrrolidin-3-yl]-methanesulfonamide.

Compounds of formula I* may be substituted by n $R^1$ selected from the group consisting of halogen, halogen-$(C_1-C_6)$-alkyl, cyano, $(C_1-C_6)$-alkoxy or halogen-$(C_1-C_6)$-alkoxy, wherein n denotes an integer selected from 0, 1, 2 and 3. Preferably n is 1 or 2.

Preferred compounds of formula I* are those, wherein $R^1$ is halogen or halogen-$(C_1-C_6)$-alkyl. Especially preferred are those compounds of formula I*, wherein $R^1$ is fluorine, chlorine or trifluoromethyl. Where the compounds of formula I* are substituted by two or three $R^1$, each $R^1$ can be the same or different.

In one embodiment the invention provides compounds of formula I wherein —X—Y— is —$CH_2$—O—. In another embodiment the invention provides compounds of formula I wherein —X—Y— is —$CH_2$—$CH_2$— or —CH═CH—.

In one embodiment the invention provides compounds of formula I wherein $R^1$, $R^{1.1}$ and $R^{1.2}$ independently from each other are selected from the group consisting of hydrogen, halogen, methyl, halogenmethyl, cyano, methoxy or halogen-methoxy. In another embodiment the present invention provides compounds of formula I wherein $R^1$, $R^{1.1}$ and $R^{1.2}$ are halogen, e.g. fluoro, e.g. 2,4,6-trifluoro, 2,4,5-trifluoro, 2,3,6-trifluoro, 2,3,4-trifluoro or 3,4,5-trifluoro. In still another embodiment the present invention provides compounds of formula I wherein $R^{1.2}$ is hydrogen and $R^1$ and $R^{1.1}$ independently from each other are selected from the group consisting of hydrogen, halogen, $(C_1-C_6)$-alkyl, halogen-$(C_1-C_6)$alkyl, cyano, $(C_1-C_6)$-alkoxy or halogen-$(C_1-C_6)$-alkoxy. In still another embodiment the present invention provides compounds of formula I wherein $R^{1.2}$ is hydrogen and $R^1$ and $R^{1.1}$ independently from each other are selected from the group consisting of halogen and $(C_1-C_6)$-alkyl. In still another embodiment the present invention provides compounds of formula I wherein $R^{1.2}$ is hydrogen, $R^{1.1}$ is halogen and $R^1$ is halogen or $(C_1-C_6)$-alkyl. In still another embodiment the present invention provides compounds of formula I wherein $R^{1.1}$ and $R^{1.2}$ are hydrogen and $R^1$ is halogen, $(C_1-C_6)$-alkyl, halogen-$(C_1-C_6)$-alkyl, cyano, $(C_1-C_6)$-alkoxy or halogen-$(C_1-C_6)$-alkoxy. In still another embodiment the present invention provides compounds of formula I wherein $R^{1.1}$ and $R^{1.2}$ are hydrogen and $R^1$ is halogen, methyl, halogenmethyl, cyano, methoxy or halogen-methoxy. In still another embodiment the present invention provides compounds of formula I wherein $R^{1.1}$ and $R^{1.2}$ are hydrogen and $R^1$ is fluoro, e.g. 3-fluoro or 4-fluoro, chloro, e.g. 3-chloro, halogenmethyl, e.g. 3-trifluoromethyl or 4-trifluoromethyl, cyano, methoxy, e.g. 2-methoxy, 3-methoxy or 4-methoxy, or halogen-methoxy, e.g. 3-trifluoromethoxy. In another embodiment the present invention provides compounds of formula I wherein $R^1$, $R^{1.1}$ and $R^{1.2}$ are hydrogen.

In one embodiment the present invention provides compounds of formula I wherein $R^{21}$, $R^{22}$ and $R^{23}$ are hydrogen.

In one embodiment the present invention provides compounds of formula I wherein $R^{24}$ is hydrogen.

In one embodiment the present invention provides compounds of formula I wherein $R^4$ is —$CONHR^5$, wherein $R^5$ is hydrogen or $(C_1-C_3)$-alkyl. In another embodiment the present invention provides compounds of formula I wherein $R^4$ is —$CONHR^5$, wherein $R^5$ is hydrogen or methyl.

In one embodiment the present invention provides compounds of formula I wherein $R^4$ is —CN.

In one embodiment the present invention provides compounds of formula I wherein $R^4$ is —$NHR^6$, wherein $R^6$ is —CO—H, —CO—$(C_1-C_6)$-alkyl, —CO-halogen-$(C_1-C_3)$-alkyl, —CO—O—$(C_1-C_3)$-alkyl, —CO—$NH_2$ or —$SO_2$—$(C_1-C_6)$-alkyl. In another embodiment the present invention provides compounds of formula I wherein $R^4$ is —$NHR^6$, wherein $R^6$ is —CO—H, —CO—$(C_1-C_6)$-alkyl, —CO—O—$(C_1-C_3)$-alkyl, —CO—$NH_2$ or —$SO_2$—$(C_1-C_6)$-alkyl. In still another embodiment the present invention provides compounds of formula I wherein $R^4$ is —$NHR^6$, wherein $R^6$ is —CO—H, —CO-methyl, —CO—O-methyl, —CO—$NH_2$ or —$SO_2$-methyl.

In one aspect the present invention provides compounds of formula I wherein the compounds have (S)-configuration. In one aspect the present invention provides compounds of formula I wherein the compounds have (R)-configuration.

In one embodiment the present invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; $R^{24}$ is hydrogen and $R^4$ is —$CONHR^5$, wherein $R^5$ is hydrogen or $(C_1-C_3)$-alkyl.

In one embodiment the present invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy. Preferably, the invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; $R^{24}$ is hydrogen. More preferably, the invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; $R^{24}$ is hydrogen; and $R^4$ is —CN.

In one embodiment the present invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy. Preferably, the invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; and $R^{24}$ is hydrogen. More preferably, the invention provides compounds of formula I wherein X—Y is —$CH_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; $R^{24}$ is hydrogen and $R^4$ is —$NHR^6$, wherein $R^6$ is —CO—H, —CO—$(C_1-C_6)$-alkyl, —CO-halogen-$(C_1-C_3)$-alkyl, —CO—O—$(C_1-C_3)$-alkyl, —CO—$NH_2$ or —$SO_2$—$(C_1-C_6)$-alkyl.

In one embodiment the present invention provides compounds of formula I wherein X—Y is —$CH_2$—O—; $R^{1.2}$ is hydrogen and $R^1$ and $R^{1.1}$ independently from each other are selected from the group consisting of hydrogen, halogen, $(C_1-C_6)$-alkyl, halogen-$(C_1-C_6)$-alkyl, cyano, $(C_1-C_6)$-alkoxy or halogen-$(C_1-C_6)$-alkoxy; $R^{21}$, $R^{22}$ and $R^{23}$ are hydrogen; $R^{24}$ is hydrogen; and $R^4$ is —$CONHR^5$, wherein $R^5$ is hydrogen or $(C_1-C_3)$-alkyl.

In one embodiment the present invention provides compounds of formula I wherein X—Y is —$CH_2$—O—; $R^{1.1}$ and $R^{1.2}$ are hydrogen and $R^1$ is halogen, $(C_1-C_6)$-alkyl, halogen-$(C_1-C_6)$-alkyl, cyano, $(C_1-C_6)$-alkoxy or halogen- ($C_1$–$C_6$)-alkoxy; $R^{21}$, $R^{22}$ and $R^{23}$ are hydrogen; $R^{24}$ is hydrogen; and $R^4$ is —CONHR$^5$, wherein $R^5$ is hydrogen or ($C_1$–$C_3$)-alkyl.

In one embodiment the present invention provides compounds of formula I wherein X—Y is —CH$_2$—O—; $R^1$, $R^{1.1}$ and $R^{1.2}$ are hydrogen; $R^{21}$, $R^{22}$ and $R^{23}$ are hydrogen; $R^{24}$ is hydrogen; and $R^4$ is —CONHR$^5$, wherein $R^5$ is hydrogen or ($C_1$–$C_3$)-alkyl.

In one embodiment the present invention provides compounds of formula I wherein X—Y is —CH$_2$—O—; $R^{1.2}$ is hydrogen and $R^1$ and $R^{1.1}$ independently from each other are selected from the group consisting of hydrogen, halogen, ($C_1$–$C_6$)-alkyl, halogen-($C_1$–$C_6$)-alkyl, cyano, ($C_1$–$C_6$)-alkoxy or halogen-($C_1$–$C_6$)-alkoxy; $R^{21}$, $R^{22}$ and $R^{23}$ are hydrogen; $R^{24}$ is hydrogen; and $R^4$ is —CN.

In one embodiment the present invention provides compounds of formula I wherein X—Y is —CH$_2$—O—; $R^{1.1}$ and $R^{1.2}$ are hydrogen and $R^1$ is halogen, ($C_1$–$C_6$)-alkyl, halogen-($C_1$–$C_6$)-alkyl, cyano, ($C_1$–$C_6$)-alkoxy or halogen-($C_1$–$C_6$)-alkoxy; $R^{21}$, $R^{22}$ and $R^{23}$ are hydrogen; $R^{24}$ is hydrogen; and $R^4$ is —CN.

In one embodiment the present invention provides compounds of formula I wherein X—Y is —CH$_2$—O—; $R^1$, $R^{1.1}$ and $R^{1.2}$ are hydrogen; $R^{21}$, $R^{22}$ and $R^{23}$ are hydrogen; $R^{24}$ is hydrogen; and $R^4$ is —CN.

In one embodiment the present invention provides compounds of formula I wherein X—Y is —CH$_2$—O—; $R^{1.2}$ is hydrogen and $R^1$ and $R^{1.1}$ independently from each other are selected from the group consisting of hydrogen, halogen, ($C_1$–$C_6$)-alkyl, halogen-($C_1$–$C_6$)-alkyl, cyano, ($C_1$–$C_6$)-alkoxy or halogen-($C_1$–$C_6$)-alkoxy; $R^{21}$, $R^{22}$ and $R^{23}$ are hydrogen; $R^{24}$ is hydrogen; and $R^4$ is —NHR$^6$, wherein $R^6$ is —CO—H, —CO—($C_1$–$C_6$)-alkyl, —CO-halogen-($C_1$–$C_3$)-alkyl, —CO—O—($C_1$–$C_3$)-alkyl, —CO—NH$_2$ or —SO$_2$—($C_1$–$C_6$)-alkyl.

In one embodiment the present invention provides compounds of formula I wherein X—Y is —CH$_2$—O—; $R^{1.1}$ and $R^{1.2}$ are hydrogen and $R^1$ is halogen, ($C_1$–$C_6$)-alkyl, halogen-($C_1$–$C_6$)-alkyl, cyano, ($C_1$–$C_6$)-alkoxy or halogen-($C_1$–$C_6$)-alkoxy; $R^{21}$, $R^{22}$ and $R^{23}$ are hydrogen; $R^{24}$ is hydrogen; and $R^4$ is —NHR$^6$, wherein $R^6$ is —CO—H, —CO—($C_1$–$C_6$)-alkyl, —CO-halogen-($C_1$–$C_3$)-alkyl, —CO—O—($C_1$–$C_3$)-alkyl, —CO—NH$_2$ or —SO$_2$—($C_1$–$C_6$)-alkyl.

In one embodiment the present invention provides compounds of formula I wherein X—Y is —CH$_2$—O—; $R^1$, $R^{1.1}$ and $R^{1.2}$ are hydrogen; $R^{21}$, $R^{22}$ and $R^{23}$ are hydrogen; $R^{24}$ is hydrogen; and $R^4$ is —NHR$^6$, wherein $R^6$ is —CO—H, —CO—($C_1$–$C_6$)-alkyl, —CO-halogen-($C_1$–$C_3$)-alkyl, —CO—O—($C_1$–$C_3$)-alkyl, —CO—NH$_2$ or —SO$_2$—($C_1$–$C_6$)-alkyl.

In one embodiment the present invention provides compounds of formula I wherein X—Y is —CH$_2$—O—; $R^{1.1}$ and $R^{1.2}$ are hydrogen and $R^1$ is halogen; $R^{21}$, $R^{22}$ and $R^{23}$ are hydrogen; $R^{24}$ is hydrogen; and $R^4$ is —NHR$^6$, wherein $R^6$ is —CO—($C_1$–$C_6$)-alkyl. In another embodiment the present invention provides compounds of formula I wherein X—Y is —CH$_2$—O—; $R^{1.1}$, $R^{1.2}$, $R^{21}$, $R^{22}$, $R^{23}$ and $R^{24}$ are hydrogen; $R^1$ is halogen; and $R^4$ is —NHR$^6$, wherein $R^6$ is —CO-methyl.

Examples of compounds of formula I include compounds selected from
(RS)-1-(4-benzyloxy-phenyl)-2-oxo-pyrrolidine-3-carbonitrile,
(RS)-1-[4-(3-fluoro-benzyloxy)-phenyl]-2-oxo-pyrrolidine-3-carboxylic acid methylamide,
(RS)-1-[4-(3-fluoro-benzyloxy)-phenyl]-2-oxo-pyrrolidine-3-carboxylic acid amide,
(RS)-1-[4-(4-fluoro-benzyloxy)-phenyl]-2-oxo-pyrrolidine-3-carboxylic acid amide,
(RS)-1-[4-(4-fluoro-benzyloxy)-phenyl]-2-oxo-pyrrolidine-3-carboxylic acid methylamide,
(RS)-2-oxo-1-[4-(4-trifluoromethyl-benzyloxy)-phenyl]-pyrrolidine-3-carboxylic acid amide,
(RS)-2-oxo-1-[4-(4-trifluoromethyl-benzyloxy)-phenyl]-pyrrolidine-3-carboxylic acid methylamide,
(S)-N-[1-(4-benzyloxy-phenyl)-2-oxo-pyrrolidin-3-yl]-acetamide,
(S)-N-[1-(4-benzyloxy-phenyl)-2-oxo-pyrrolidin-3-yl]-methanesulfonamide,
(S)-N-{1-[4-(3-fluoro-benzyloxy)-phenyl]-2-oxo-pyrrolidin-3-yl}-acetamide,
(R)-N-{1-[4-(3-fluoro-benzyloxy)-phenyl]-2-oxo-pyrrolidin-3-yl}-acetamide,
(R)-N-{1-[4-(3-fluoro-benzyloxy)-phenyl]-2-oxo-pyrrolidin-3-yl}-methanesulfonamide,
(S)-N-{1-[4-(3-fluoro-benzyloxy)-phenyl]-2-oxo-pyrrolidin-3-yl}-methanesulfonamide,
(S)-{1-[4-(3-fluoro-benzyloxy)-phenyl]-2-oxo-pyrrolidin-3-yl}-carbamic acid methyl ester,
(R)-N-{1-[4-(3-fluoro-benzyloxy)-phenyl]-2-oxo-pyrrolidin-3-yl}-formamide,
(S)-N-{1-[4-(3-fluoro-benzyloxy)-phenyl]-2-oxo-pyrrolidin-3-yl}-formamide,
(R)-{1-[4-(3-fluoro-benzyloxy)-phenyl]-2-oxo-pyrrolidin-3-yl}-urea,
(S)-{1-[4-(3-fluoro-benzyloxy)-phenyl]-2-oxo-pyrrolidin-3-yl}-urea,
(S)-N-{1-(S)-[4-(4-fluoro-benzyloxy)-phenyl]-2-oxo-pyrrolidin-3-yl}-acetamide,
(S)-N-{1-(S)-[4-(2,6-difluoro-benzyloxy)-phenyl]-2-oxo-pyrrolidin-3-yl}-acetamide and
(S)-N-{1-[4-(3,4-difluoro-benzyloxy)-phenyl]-2-oxo-pyrrolidin-3-yl}-acetamide.

In one embodiment the present invention provides a process for the preparation of compounds of formula I wherein
(a) $R^4$ is CONHR$^5$
comprising reacting a compound of formula II

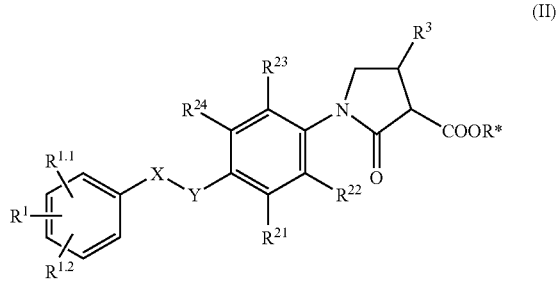

wherein $R^1$, $R^{1.1}$, $R^{1.2}$, $R^{21}$, $R^{22}$, $R^{23}$, $R^{24}$, $R^3$, X and Y have the meanings as defined above and R* is hydrogen or ($C_1$–$C_6$)-alkyl,
with an amine of formula H$_2$N—R$^5$, wherein $R^5$ has the above meaning;

(b) $R^4$ is CN comprising reacting a compound of formula III

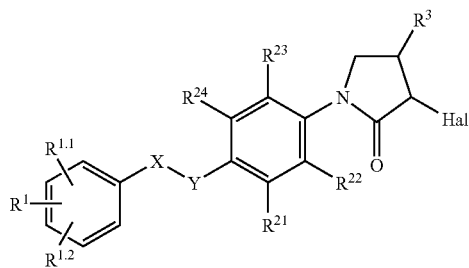

(III)

wherein $R^1$, $R^{1.1}$, $R^{1.2}$, $R^{21}$, $R^{22}$, $R^{23}$, $R^{24}$, $R^3$, X and Y have the meanings as defined above and Hal is halogen, with a cyanide salt; or (c) $R^4$ is $NHR^6$ comprising reacting a compound of formula IV

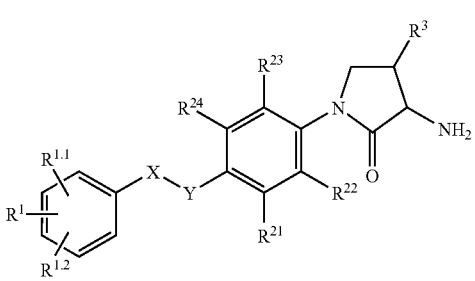

(IV)

wherein $R^1$, $R^{1.1}$, $R^{1.2}$, $R^{21}$, $R^{22}$, $R^{23}$, $R^{24}$, $R^3$, X and Y have the meanings as defined above, with an acyl donating agent of formula Z-CO—$(C_1$–$C_6)$-alkyl, Z-CO-halogen-$(C_1$–$C_3)$-alkyl, Z-CO—O—$(C_1$–$C_3)$-alkyl, or Z-SO$_2$—$(C_1$–$C_3)$-alkyl wherein Z is an activating group, e.g. a halogen or anhydride, or with an isocyanate.

The compounds of general formula I* can be manufactured by reacting a compound of formula II*

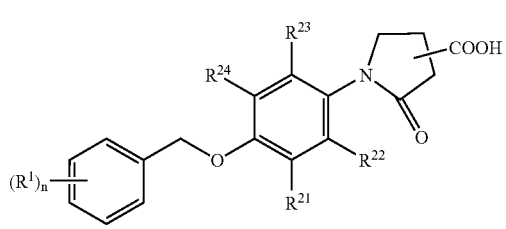

(II*)

wherein $R^1$, $R^{21}$, $R^{22}$, $R^{23}$, $R^{24}$ and n have the above meanings with an amine of formula $H_2N$—$R^5$, wherein $R^5$ has the above meaning, to obtain a compound of formula Ia*

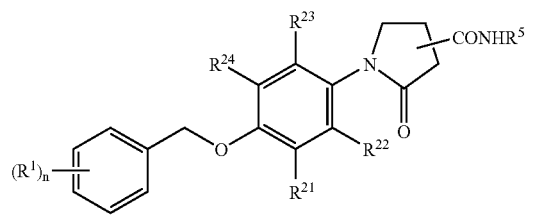

(Ia*)

or, alternatively, reducing a compound of formula II* to the corresponding alcohol of formula III*

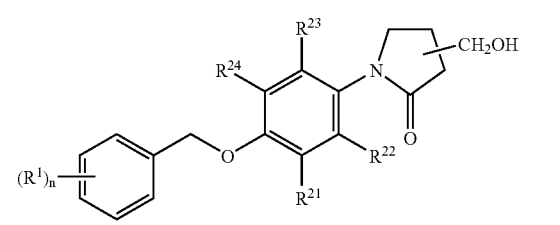

(III*)

and reacting this compound with a cyanide salt to obtain a compound of formula Ib*

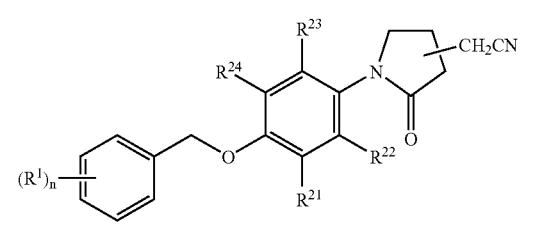

(Ib*)

or, alternatively, reacting a compound of formula IV*

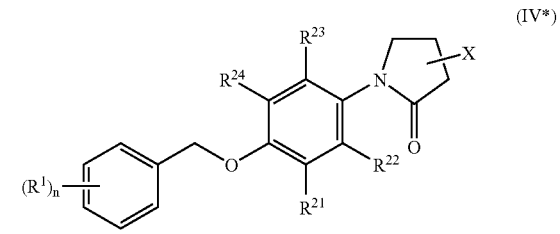

(IV*)

wherein X is halogen, with a cyanide salt, to obtain a compound of formula Ic*

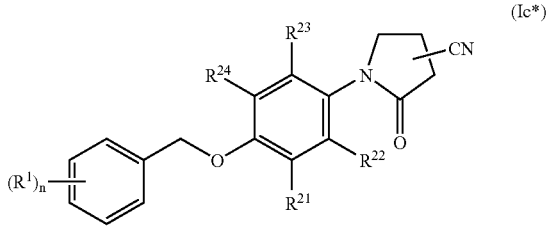

or, alternatively, reacting a compound of formula V*

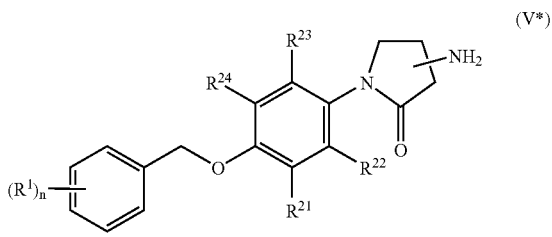

with an acylating agent of formula Y—CO—($C_1$-$C_6$)-alkyl or Y'—$SO_2$—($C_1$-$C_6$)-alkyl, wherein Y and Y' represent an activating group, e.g. a halogen, to obtain a compound of formula Id*

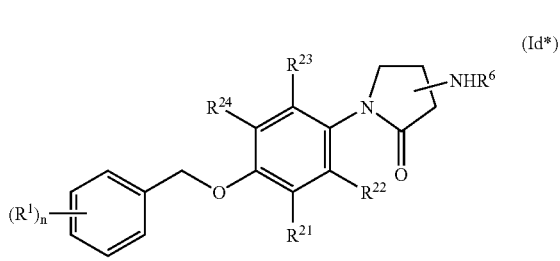

wherein $R^6$ has the above meanings.

All starting materials employed in the processes described herein are either commercially available or can be prepared by conventional means.

In accordance with the present invention, scheme 1 shows exemplary routes to compounds of the formula I, all starting from a compound of formula V. The reaction of a compound of formula V with a compound of formula VI [Ikuta et al., J. Med. Chem. 30:1995 (1987)] to obtain the intermediate of formula IIIa, may be in inert solvents like dichloromethane, ethyl acetate or ethers in the presence of a base like triethylamine or carbonate and at a temperature in the range of from 0° C. to 25° C. Cyclisation of the intermediate 2,4-dihalo-N-acyl derivative to the pyrrolidone IIIa may be with bases like sodium or potassium hydroxide in inert solvents like dichloromethane or ethers at a temperature of from 0° C. to 25° C. Intermediates II wherein R* is H, i.e. compounds of formula IIa, are prepared by reacting a compound of formula V with 6,6-dimethyl-5,7-dioxa-spiro [2,5]octane-4,8-dione VII, as described by Danishefsky et al. [J. Amer. Chem. Soc. 97:3239 (1975)].

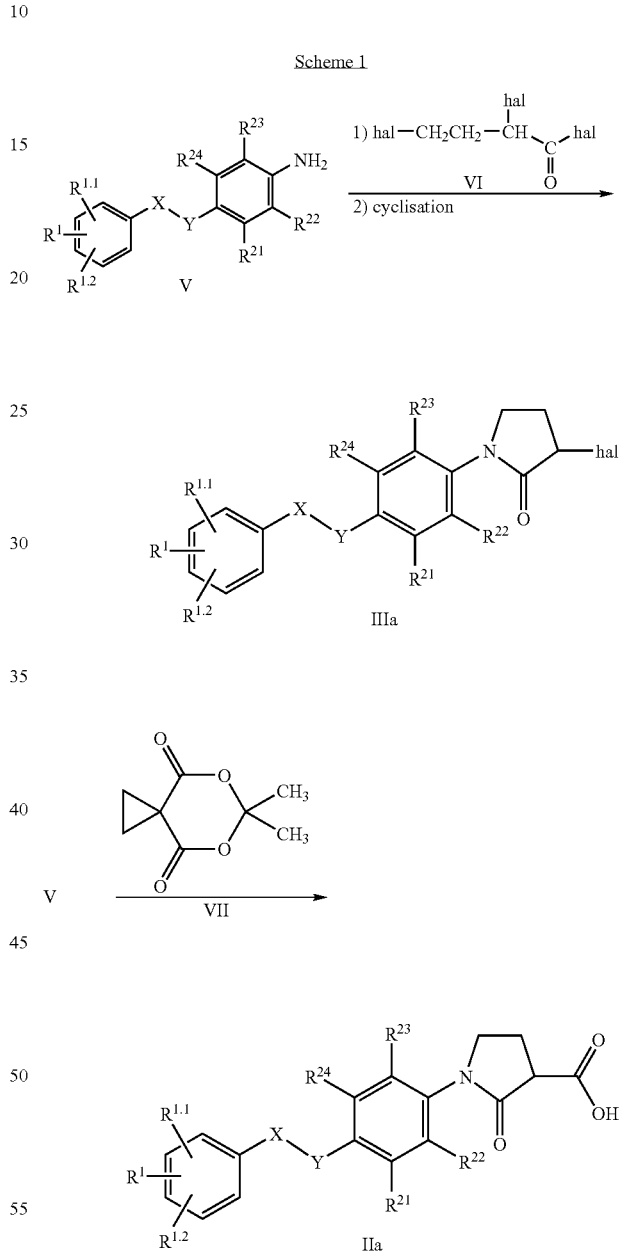

Another method to prepare compounds of formula I involves cross-coupling reactions of arylstannanes [Lam et al., Tetrahedron Lett. 43:3091 (2002)], arylboronates [Lam et al., Synlett 5:674 (2000); Chan et al., Tetrahedron Lett. 39:2933 (1998)] or aryl halides [Buchwald et al., J. Amer. Chem. Soc. 118:7215 (1996)] with the corresponding pyrrolidones (scheme 2).

Scheme 2

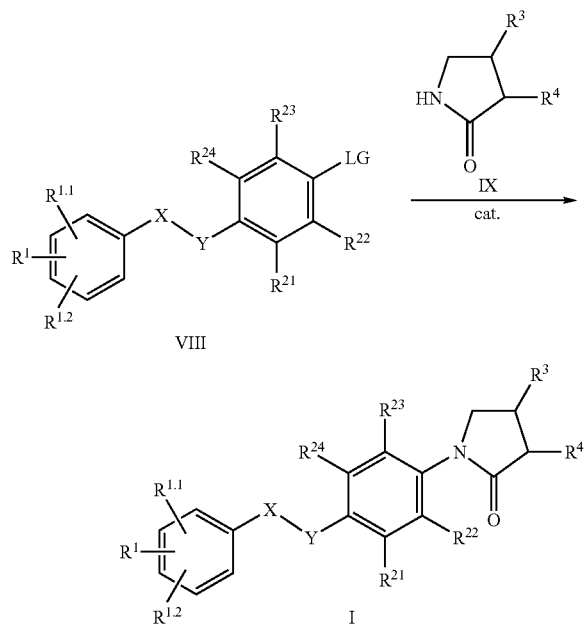

wherein LG is halogen, e.g. Cl, Br or I, or SnR$_3$ or B(OH)$_2$.

In accordance with the present invention, one method for preparing compounds of general formula V, wherein —X—Y— is —CH$_2$—O—, i.e. compounds of formula Va, is shown in scheme 3: The intermediates of formula XII are accessible through nucleophilic substitution of aromatic nitro compounds of formula XI containing p-substituted leaving groups with benzylic alcohols of formula X. Leaving groups in para-position can be, e.g., halogens (F, Cl, Br, I), tosylates, mesylates or triflates. These substitution reactions can be conducted neat or in inert solvents, for example, toluene or xylene. A preferred reaction temperature is in the range of from 50° C. to 150° C. Alternatively, compounds of formula XII can be prepared by Williamson-ether synthesis, starting from p-nitrophenols XIV and benzylic halides, tosylates, mesylates or triflates of formula XIII. Bases used can be, e.g. alcoholates or carbonates (sodium, potassium or cesium carbonate). Examples for solvents include lower alcohols, acetonitrile or lower ketones at a temperature in the range of from 20° C. to reflux temperature. Another approach is the Mitsunobu-coupling of benzylic alcohols with p-nitrophenols. The reaction is done as usual in inert solvents, for example, diethyl ether or tetrahydrofurane, using dialkyl-azo-dicarboxylates in the presence of phosphines (for example tributyl- or triphenyl-phosphine).

The key intermediates of formula XII are reduced to the amino compounds of formula Va using catalytic hydrogenation, e.g. using platinum on charcoal as the catalyst in lower alcohols, ethyl acetate or tetrahydrofurane. An alternative is the reduction of the nitro-group by metals like iron, tin, or zinc in acidic media like diluted hydrochloric acid or acetic acid. Metals can also be replaced by metal salts, e.g., tin-(II)-chloride).

Scheme 3

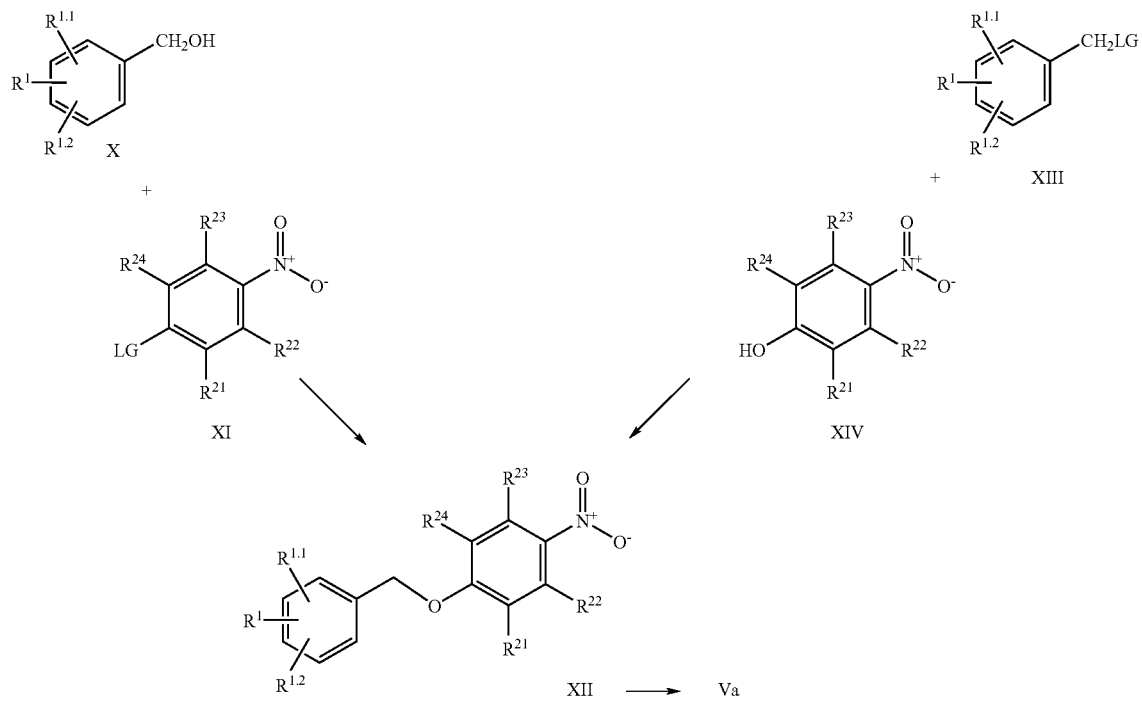

wherein LG is a leaving group, e.g. halogen and OTf, or OH (for Mitsunobu-coupling).

In accordance with the present invention, intermediates of formula Vb (wherein —X—Y— is —CH=CH—) and Vc (wherein —X—Y— is —CH$_2$—CH$_2$—) can be prepared, for example, as shown in scheme 4: The intermediates of formula XVII are accessible by olefination reaction of optionally substituted aromatic aldehydes of formula XV with dialkyl (4-nitro-benzyl)-phosphonates of formula XVI in the presence of a base, e.g. sodium hydride, yielding the corresponding nitro-olefins of formula XVII.

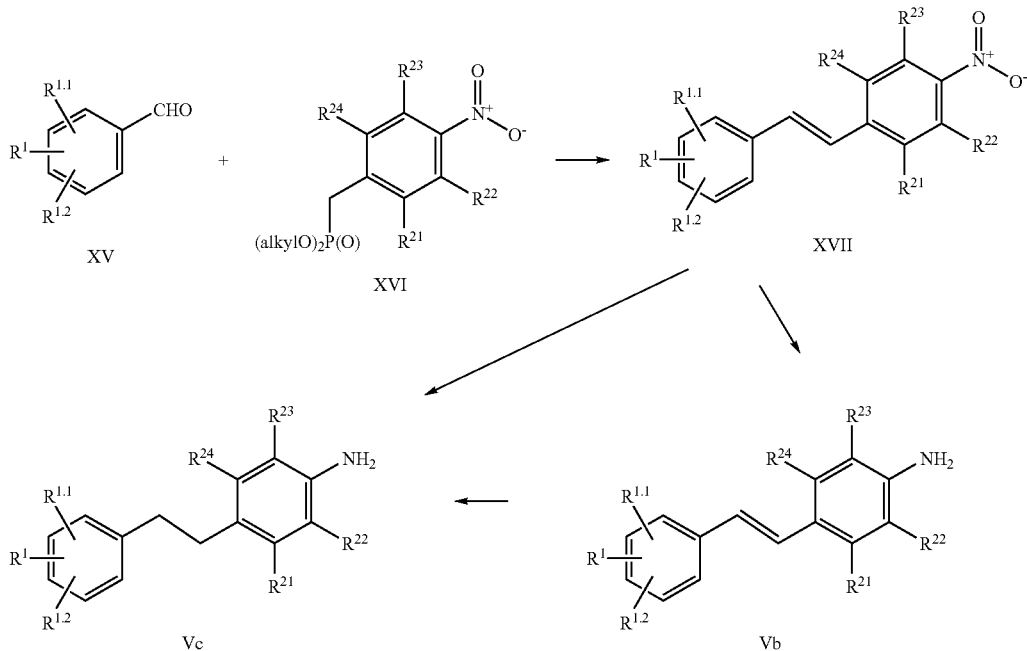

Scheme 4

The key intermediates of formula XVII can be reduced selectively to the amino-olefins of formula Vb using catalytic hydrogenation, e.g., using platinum on charcoal as the catalyst in lower alcohols, ethyl acetate or tetrahydrofurane as the solvent, or, by metals or metal salts, e.g., tin-(II)-chloride. The amino derivatives of formula Vc can be obtained directly from the nitro derivatives of formula XVII or from the amino-olefins of formula Vb by hydrogenation using palladium on charcoal as the catalyst in lower alcohols, ethyl acetate or tetrahydrofurane as the solvent.

Intermediates II can be transformed into compounds of formula I using standard procedures. The acids II are activated via acid chloride (thionyl chloride or oxalyl chloride) or with DCC, EDC etc. and subsequently coupled with the amine R$^5$—NH$_2$. Alternatively, the corresponding alkylesters can be transformed to intermediates II by aminolysis by amines of formula R$^5$—NH$_2$.

Intermediates III can be transformed into the desired compounds I wherein R$^4$ is CN, i.e. compounds of formula Ib, by reaction with sodium or potassium cyanide in solvents like N,N-dimethylformamide, acetone or acetonitrile at a temperature in the range of from 20° C. to 140° C. Catalytic amounts of sodium or potassium iodide can be added to speed up the reaction (scheme 5).

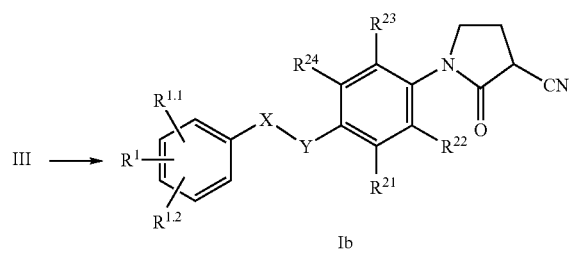

Scheme 5

Compounds of formula IV can be obtained starting from acid derivatives of formula II by nucleophilic migrations from a carbon to a nitrogen atom, such as e.g. by Hofmann or Curtius rearrangement, via the formation of the corresponding isocyanate and its treatment with suitable alcohols delivering the protected amino group, methods known per se from the literature (scheme 6). For the treatment of the intermediate isocyanate, alcohols are selected which yield the typical carbamates used as amine protecting groups, such as e.g. tert-butoxycarbonyl, benzyloxycarbonyl, or fluorenylmethoxycarbonyl. Their cleavage to the amine follows the protocols which are well known in the literature. The further transformation to compounds of formula I can be performed by standard procedures, such as e.g. by reaction with activated acyl derivatives, e.g. acyl halogenides or anhydrides, or by condensation reactions of the acid using e.g. carbodiimides as condensation reagent, or by isocyanates.

For the preparation of enantiopure derivatives of formula IV, an alternative route can be followed (scheme 7). Basically, the protocol follows the conditions described by Freidinger et al. [J. Org. Chem. 47:104–109 (1982)] where the aniline derivative of formula V is acylated by an N-protected methionine derivative in its racemic or optically active form by standard conditions of condensation reactions to give compounds of formula XIX. Methylation with methyliodide or trimethyl-sulfonium or trimethylsulfoxonium salts and treatment of the resulting dimethyl-sulfonium salt with base, such as e.g. sodium hydride or lithium or potassium bis(trimethylsilyl)amide, in solvents inert under these conditions, e.g. THF, dichloromethane or N,N-dimethylformamide, yield the cyclised N-protected product of formula XX. Another variation of this cyclisation procedure is described in EP 985,665 which refers to a process for the preparation of 3-amino-2-oxo-pyrrolidines.

Scheme 6

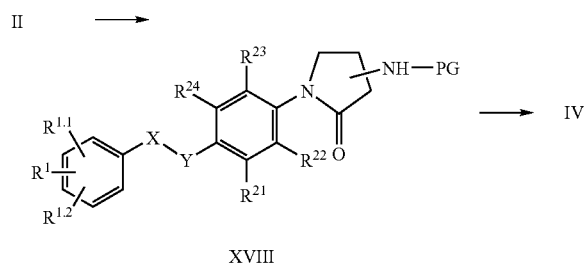

Scheme 7

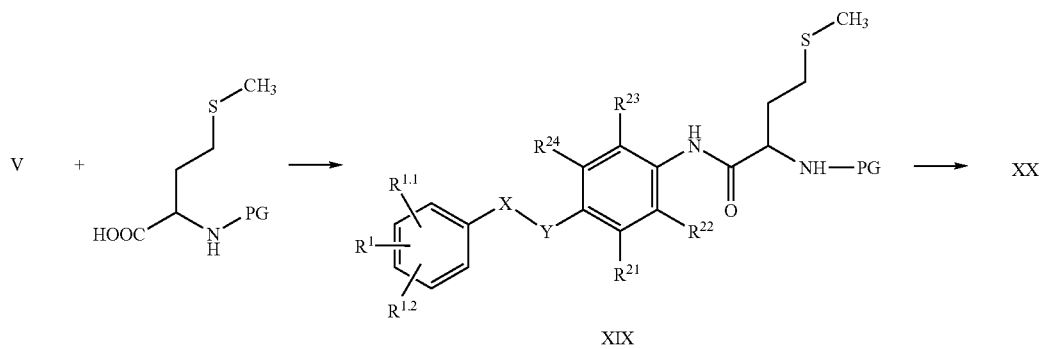

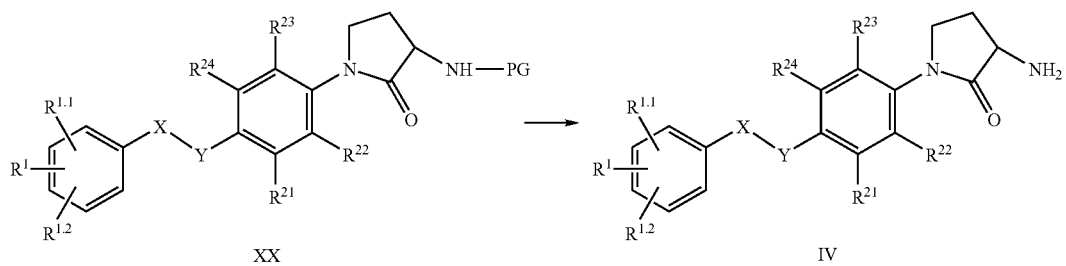

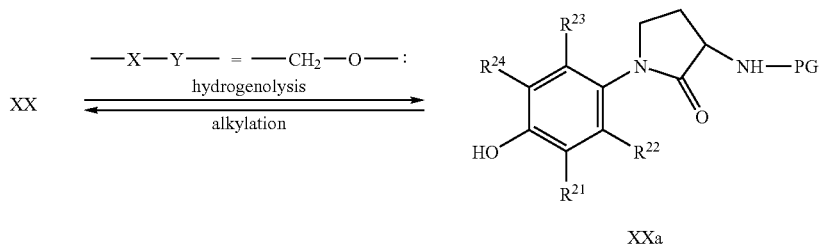

-continued

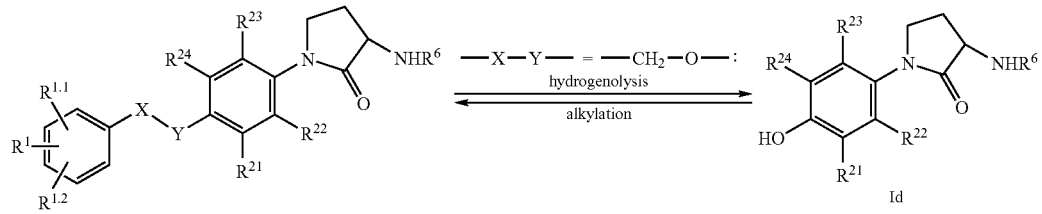

In compounds of formula I or XX where —X—Y— has the meaning of —CH$_2$—O—, the optionally substituted benzyl residue can function as a transient group which can be cleaved by hydrogenolysis. The resulting phenols Id and XXa can then be re-alkylated by a different benzyl group under the aforementioned conditions. As known to those skilled in the art, this process is only possible on condition that R$^6$ and PG are representing groups that are stable under the aforementioned reaction conditions for the hydrogenolysis and alkylation reaction, e.g. formyl or acetyl for R$^6$, tert-butoxycarbonyl (BOC) for PG.

Compounds of general formula I can also exist in optically pure form. Such optically pure compounds can be prepared from enantiopure compounds from the chiral pool, e.g., (R)- or (S)-methionine as already described for the preparation of enantiopure derivatives of formula IV (scheme 7). In other cases, separation into antipodes can be affected according methods known per se, either preferably at an early stage of the synthesis starting with compounds of formula II by salt formation with an optically active amine such as, for example, (+)- or (−)-1-phenylethylamine and separation of the diastereomeric salts by fractional crystallisation or preferably by derivatisation with a chiral auxiliary substance such as, for example, (+)- or (−)-2-butanol, (+)- or (−)-1-phenylethanol, or (+)- or (−)-menthol and separation of the diastereomeric products by chromatography and/or crystallisation and subsequent cleavage of the bond to the chiral auxiliary substance. In order to determine the absolute configuration of the pyrrolidinone derivative obtained, the pure diastereomeric salts and derivatives can be analysed by conventional spectroscopic methods, with X-ray spectroscopy on single crystals being an especially suitable method.

The Active Compounds are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease.

Other indications include psychiatric diseases such as depression, anxiety, panic attack, social phobia, schizophrenia, eating and metabolic disorders such as obesity, as well as the prevention and treatment of withdrawal syndromes induced by abuse of alcohol, nicotine and other addictive drugs. Other treatable indications may be peripheral neuropathy caused by cancer chemotherapy (WO 97/33,572), reward deficiency syndrome (WO 01/34,172), or the treatment of multiple sclerosis (WO 96/40,095), and other neuroinflammatory diseases.

The Active Compounds are especially useful for the treatment and prevention of Alzheimer's disease and senile dementia.

The pharmacological activity of the compounds was tested using the following method:

The cDNAs encoding human MAO-A and MAO-B were transiently transfected into EBNA cells using the procedure described by Schlaeger and Christensen [Cytotechnology 15:1–13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169–174 (1997)]. Briefly, membrane aliquots were incubated in 0.1 M potassium phosphate buffer, pH 7.4, for 30 min at 37° C. containing different concentrations of the compounds. After this period, the enzymatic reaction was started by the addition of the MAO substrate tyramine together with 1 U/ml horse-radish peroxidase (Roche Biochemicals) and 80 µM N-acetyl-3,7-dihydroxyphenoxazine (Amplex Red, Molecular Probes). The samples were further incubated for 30 min at 37° C. in a final volume of 200 µl and absorbance was then determined at a wavelength of 570 nm using a SpectraMax plate reader (Molecular Devices). Background (non-specific) absorbance was determined in the presence of 10 µM clorgyline for MAO-A or 10 µM L-deprenyl for MAO-B. IC$_{50}$ values were determined from inhibition curves obtained using nine inhibitor concentrations in duplicate, by fitting data to a four parameter logistic equation using a computer program.

The compounds of the present invention are specific MAO-B inhibitors. The IC$_{50}$ values of preferred Active Compounds as measured in the assay described above are in the range of 1 µM or less, typically 0.1 µM or less, and ideally 0.02 µM or less.

The present invention also provides pharmaceutical compositions containing Active Compounds, or pharmaceutically acceptable salts thereof, and a pharmaceutically acceptable carrier. Active Compounds includes individual isomers and racemic and nonracemic mixtures thereof. Such pharmaceutical compositions can be in the form of tablets, coated tablets, dragées, hard and soft gelatine capsules, solutions, emulsions or suspensions. The pharmaceutical compositions can also be in the form of suppositories or injectable solutions.

The pharmaceutical compositions of the invention, in addition to one or more Active Compounds, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of Active Compounds, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the invention are selective MAO-B inhibitors. Therefore, the present invention also provides methods of treating or preventing diseases that are mediated by monoamine oxidase B. Such methods include administering a therapeutically effective amount of an Active Compound, for example, a compound of formula I or I*, or a pharmaceutically acceptable salt thereof, to an individual in need of such treatment. In one embodiment, the invention provides a method for the treatment or prevention of Alzheimer's disease by administering to an individual a therapeutically effective amount of an Active Compound, e.g., a compound of formula I or I*. In another embodiment, the present invention provides a method for the treatment or prevention of senile dementia by administering to an individual a therapeutically effective amount of an Active Compound, e.g., a compound of formula I or I*.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

The dosage at which the Active Compound is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. Unless otherwise indicated, the following examples have been performed, regardless of the tense in which they are written. The abbreviation "RT" means "room temperature".

EXAMPLE 1

(RS)-1-(4-Benzyloxy-phenyl)-2-oxo-pyrrolidine-3-carbonitrile a) (RS)—N-(4-Benzyloxy-phenyl)-2,4-dibromo-butyramide A solution of 12.8 g (64.2 mmol) 4-benzyloxyaniline and 9.74 g (96.3 mmol) triethylamine in 125 ml dichloromethane is cooled to 0° C. 20.4 g (77.1 mmol) of 2,4-dibromobutyryl chloride [Ikuta et al., J. Med. Chem. 30:1995 (1987)] is slowly added over a period of 45 min. The reaction mixture is stirred for additional 15 min, then hydrolysed with 100 ml of water. The insoluble precipitate is filtered off and the organic phase is washed successively with a saturated solution of sodium hydrogencarbonate and water. After drying and evaporation, the crude product is subjected to chromatography (silica gel, dichloromethane) to yield 6.1 g (22%) of a colorless solid. Mp=139.5–142° C.

b) (RS)-1-(4-Benzyloxy-phenyl)-3-bromo-pyrrolidin-2-one 6.1 g (14.3 mmol) (RS)—N-(4-benzyloxy-phenyl)-2,4-dibromo-butyramide and 0.1 g of Dowex 2×10 are suspended in 50 ml dichloromethane. 7 ml of a 50% aqueous sodium hydroxide solution is slowly added under vigorous stirring. The resulting reaction mixture is stirred overnight at RT, then poured into 25 ml of cold water. The organic phase is separated, dried and evaporated. The crude material is recrystallised from ethyl acetate to yield 1.72 g (35%) of a brownish solid. Mp=125–126° C.

c) (RS)-1-(4-Benzyloxy-phenyl)-2-oxo-pyrrolidine-3-carbonitrile 300 mg (0.87 mmol) of (RS)-1-(4-benzyloxy-phenyl)-3-bromo-pyrrolidin-2-one is dissolved in 5 ml N,N-dimethylformamide. 64 mg (1.3 mmol) sodium cyanide and 13 mg (0.09 mmol) sodium iodide are added and the suspension stirred for 10 min. at 120° C. The reaction mixture is treated with water and extracted with ethyl acetate to yield 33 mg (13%) of a colorless solid. MS: m/e=293.3 $(M+H)^+$.

EXAMPLE 2

(RS)-1-[4-(3-Fluoro-benzyloxy)-phenyl]-2-oxo-pyrrolidine-3-carboxylic Acid Methylamide a) 1-(4-Benzyloxy-phenyl)-pyrrolidin-2-one 20.3 g (101.9 mmol) 4-benzyloxyaniline and 9.1 ml (119.2 mmol) gamma-butyro-lactone are treated with 3 ml concentrated hydrochloric acid. The mixture is heated 20 hours to 160° C., then 5.5 hours to 200° C. After cooling, the mixture is extracted with 250 ml ethyl acetate, washed with saturated aqueous sodium hydrogencarbonate and dried. Evaporation of the solvent and recrystallisation from diethyl ether yields 8.4 g (31%) of a brownish solid. MS: m/e=267 $(M^+)$.

b) 1-(4-Hydroxy-phenyl)-pyrrolidin-2-one 6.2 g (23.2 mmol) 1-(4-benzyloxy-phenyl)-pyrrolidin-2-one is dissolved in 200 ml THF. 3 drops of acetic acid are added and the solution is hydrogenated for 5 hours at RT and normal pressure in presence of 0.62 g palladium 10% on charcoal. Filtration and concentration gives a semisolid material. Chromatography (silica gel, dichloromethane/methanol 95:5) yields 2.73 g (66%) of a brownish solid. MS: m/e=175.9 (M−H).

c) 1-[4-(3-Fluoro-benzyloxy)-phenyl]-pyrrolidin-2-one

A mixture of 2.73 g (15.4 mmol) of 1-(4-hydroxy-phenyl)-pyrrolidin-2-one, 3.2 g (16.9 mmol) of 3-fluorobenzylbromide and 4.26 g (31 mmol) of potassium carbonate in 100 ml of 2-butanone is heated at 80° C. for 18 hours. After cooling to RT, the reaction mixture is treated with water and ethyl acetate. The organic layer is separated, dried over magnesium sulfate and evaporated under reduced pressure. The solid residue is crystallised from ether to yield 3.86 g (88% of theory) of 1-[4-(3-fluoro-benzyloxy)-phenyl]-pyrrolidin-2-one as a colorless solid. MS: m/e=286.0 (M+H)$^+$.

d) 1-[4-(3-Fluoro-benzyloxy)-phenyl]-2-oxo-pyrrolidine-3-carboxylic Acid Ethyl Ester 370 mg (15.4 mmol) sodium hydride is suspended in 20 ml THF and 911 mg (7.7 mmol) diethylcarbonate is added. The suspension is heated to reflux temperature. A solution of 2.0 g (7.0 mmol) 1-[4-(3-Fluoro-benzyloxy)-phenyl]-pyrrolidin-2-one in 10 ml THF is slowly added into the boiling solution. The mixture is boiled for another 5 hours, then hydrolysed with cold water and washed successively with water, saturated sodium hydrogencarbonate solution, water and saturated sodium chloride solution. Chromatography (silica gel, dichloromethane/ethyl acetate) yields 1.3 g (52%) of a yellowish semisolid. MS: m/e=358.2 (M+H)$^+$.

e) (RS)-1-[4-(3-Fluoro-benzyloxy)-phenyl]-2-oxo-pyrrolidine-3-carboxylic Acid Methylamide 300 mg (0.84 mmol) 1-[4-(3-Fluoro-benzyloxy)-phenyl]-2-oxo-pyrrolidine-3-carboxylic acid ethyl ester is dissolved in 2 ml N,N-dimethylformamide. 0.17 ml (4.2 mmol) of a 33% solution of methylamine in ethanol is added. The reaction vessel is tightly stoppered and heated to 120° C. for 24 hours. Addition of water precipitates the crude material. Chromatography (silica gel, dichloromethane/methanol) yields 41 mg (14%) of a yellowish solid. MS: m/e=343.2 (M+H)$^+$.

EXAMPLE 3

(RS)-1-[4-(3-Fluoro-benzyloxy)-phenyl]-2-oxo-pyrrolidine-3-carboxylic Acid Amide a) 1-(3-Fluorobenzyloxy)-4-nitro-benzene A mixture of 5.04 g (40 mmol) 3-fluorobenzyl alcohol and 1.29 g (4 mmol) tris-(dioxa-3,6-heptyl)amine is treated with 2.47 g (44 mmol) of potassium hydroxide. The mixture is stirred at RT for 10 min, then 5.55 g (44 mmol) of 4-fluoronitrobenzene is slowly added through a dropping funnel. The mixture is kept for 45 min at 80° C., cooled to RT and diluted with about 75 ml water. Extraction with ethyl acetate and washing with 2M aqueous hydrochloric acid yields a yellowish organic phase, which is dried and evaporated. The residue is recrystallised from methanol to give 6.07 g (61%) of the title compound. Yellow crystals, mp=104–105° C.

b) 4-(3-Fluoro-benzyloxy)-phenylamine 3 g (12.1 mmol) of 1-(3-fluorobenzyloxy)-4-nitro-benzene is dissolved in 125 ml of methanol. 150 mg of Pt 5% on charcoal is added and hydrogenation done under normal pressure for about 17 h. The catalyst is filtered and the solution evaporated to yield 2.51 g (95%) of crude brownish material. MS: m/e=218.4 (M+H)$^+$.

c) (RS)-1-[4-(3-Fluoro-benzyloxy)-phenyl]-2-oxo-pyrrolidine-3-carboxylic Acid

A solution of 561 mg (2.6 mmol) 4-(3-fluoro-benzyloxy)-phenylamine and 448 mg (2.6 mmol) 6,6-dimethyl-5,7-dioxa-spiro[2,5]octane-4,8-dione in 2 ml dichloromethane is refluxed for 16 hours. 5 ml of diethylether is added and the precipitate filtered off to yield 485 mg (57%) of a colorless solid. MS: m/e=330.2 (M+H)$^+$.

d) (RS)-1-[4-(3-Fluoro-benzyloxy)-phenyl]-2-oxo-pyrrolidine-3-carboxylic Acid Amide 300 mg (0.91 mmol) (RS)-1-[4-(3-fluoro-benzyloxy)-phenyl]-2-oxo-pyrrolidine-3-carboxylic acid is dissolved in 2 ml dichloromethane plus 2 drops of N,N-dimethylformamide. The solution is cooled to 0° C. and treated with 173 mg (1.37 mmol) oxalyl chloride. After 1 hour at 0° C. the solvent is removed under vacuum at RT. The residue is taken up in 1 ml dichloromethane and slowly added to a mixture of 2 ml THF and 5 ml concentrated ammonia. Stirring is continued for 1 hour at RT. Evaporation of the solvents and dilution with water yields a precipitate, which is filtered off. Recrystallisation from methanol yields 112 mg (37%) of a colorless solid. MS: m/e=329.2 (M+H)$^+$.

EXAMPLE 4

(RS)-1-[4-(4-Fluoro-benzyloxy)-phenyl]-2-oxo-pyrrolidine-3-carboxylic Acid Amide a) 1-(4-Fluorobenzyloxy)-4-nitro-benzene The title compound is prepared in analogy to Example 3a) from 4-fluorobenzyl alcohol and 4-fluoro-nitrobenzene. Yield: 86% of a yellowish solid. Mp=124–126° C.

b) 4-(4-Fluoro-benzyloxy)-phenylamine

The title compound is prepared in analogy to Example 3b) by reduction of 1-(4-fluorobenzyloxy)-4-nitro-benzene. Yield: 98% of a red solid. MS: m/e=218.3 (M+H)$^+$.

c) (RS)-1-[4-(4-Fluoro-benzyloxy)-phenyl]-2-oxo-pyrrolidine-3-carboxylic Acid

The title compound is prepared in analogy to Example 3c) from 4-(4-fluoro-benzyloxy)-phenylamine and 6,6-dimethyl-5,7-dioxa-spiro[2,5]octane-4,8-dione. Yield: 56% of a colorless solid. MS: m/e=284.1 (M−CO$_2$).

d) (RS)-1-[4-(4-Fluoro-benzyloxy)-phenyl]-2-oxo-pyrrolidine-3-carboxylic Acid Amide The title compound is prepared in analogy to Example 3d) from (RS)-1-[4-(4-fluoro-benzyloxy)-phenyl]-2-oxo-pyrrolidine-3-carboxylic acid and ammonia. Yield: 18% of a brownish solid. MS: m/e=329.3 (M$^+$+H).

EXAMPLE 5

(RS)-1-[4-(4-Fluoro-benzyloxy)-phenyl]-2-oxo-pyrrolidine-3-carboxylic Acid Methylamide The title compound is prepared in analogy to Example 3d) from (RS)-1-[4-(4-fluoro-benzyloxy)-phenyl]-2-oxo-pyrrolidine-3-carboxylic acid and methylamine. Yield: 17% of a colorless solid. MS: m/e=343.2 (M+H)$^+$.

EXAMPLE 6

(RS)-2-Oxo-α-[4-(4-trifluoromethyl-benzyloxy)-phenyl]-pyrrolidine-3-carboxylic Acid Amide a) 1-(4-Trifluoromethyl-benzyloxy)-4-nitro-benzene The title compound is prepared in analogy to Example 3a) from 4-fluoro-nitro-benzene and 4-trifluoromethyl-benzyl alcohol. Yield 82% of a slightly brown solid. Mp.=80.5–81.5° C.

b) 4-(4-Trifluoromethyl-benzyloxy)-phenylamine

The title compound is prepared in analogy to Example 3b) by reduction of 1-(4-trifluoromethyl-benzyloxy)-4-nitro-benzene. Yield: 91% of a yellowish solid. MS: m/e=268.3 (M+H)$^+$.

c) (RS)-2-Oxo-1-[4-(4-trifluoromethyl-benzyloxy)-phenyl]-pyrrolidine-3-carboxylic Acid The title compound is prepared in analogy to Example 3c) from 4-(4-trifluoromethyl-benzyloxy)-phenylamine and 6,6-dimethyl-5,7-dioxa-spiro[2,5]octane-4,8-dione. Yield: 37% of a colorless solid. MS: m/e=380.1 (M+H)$^+$.

d) (RS)-2-Oxo-1-[4-(4-trifluoromethyl-benzyloxy)-phenyl]-pyrrolidine-3-carboxylic Acid Amide 150 mg (0.4 mmol) (RS)-2-oxo-1-[4-(4-trifluoromethyl-benzyloxy)-phenyl]-pyrrolidine-3-carboxylic acid is dissolved in 4 ml THF. 59 mg (0.43 mmol) of 1-hydroxybenzotriazole and 80 mg (0.42 mmol) of N-(3-dimethylaminopropyl)-N'-ethyl-carbodiimide-hydrochloride is added and the reaction mixture is stirred at RT for 30 min. After cooling to 0° C. 4 ml of concentrated ammonia is added and the resulting mixture stirred at RT for 1 hour. Dilution with water, extraction and chromatography (silica gel, ethyl acetate) yields 15 mg (10%) of a colorless solid. MS: m/e=379.2 (M+H)$^+$.

EXAMPLE 7

(RS)-2-Oxo-1-[4-(4-trifluoromethyl-benzyloxy)-phenyl]-pyrrolidine-3-carboxylic Acid Methylamide The title compound is prepared in analogy to Example 6d) from (RS)-2-oxo-1-[4-(4-trifluoromethyl-benzyloxy)-phenyl]-pyrrolidine-3-carboxylic acid and methylamine. Yield: 6% of a colorless solid. MS: m/e=393.2 (M+H)$^+$.

EXAMPLE 8

(S)-N-[1-(4-Benzyloxy-phenyl)-2-oxo-pyrrolidin-3-yl]-acetamide a) (S)-[1-(4-Benzyloxy-phenylcarbamoyl)-3-methylsulfanyl-propyl]-carbamic Acid Tert-Butyl Ester A solution of 0.57 g (2.3 mmol) of (S)-Boc-methionine in 5 ml of dichloromethane is treated at RT consecutively with 0.87 g (2.3 mmol) of O-(benzotriazol-1-yl)-N,N,N',N'-tetramethyluronium-hexafluorophosphate (HBTU), 0.50 g (2.1 mmol) of 4-benzyloxyaniline hydrochloride and 0.98 ml (5.7 mmol) of N-ethyl-diisopropylamine. The reaction mixture is stirred during 1 h at RT. For the working-up, the reaction mixture is diluted with dichloromethane and treated with 20 ml of an aqueous solution of citric acid (10%). The aqueous phase is re-extracted with dichloromethane, the organic phases combined, dried over sodium sulfate and evaporated under reduced pressure. For purification, the crude material obtained is chromatographed on silica gel using a 3:1 mixture of n-hexane and ethyl acetate as the eluent. There are obtained 0.74 g (82.5% of theory) of (S)-[1-(4-benzyloxy-phenylcarbamoyl)-3-methylsulfanyl-propyl]-carbamic acid tert-butyl ester as a white solid. MS: m/e=431 (M+H)$^+$.

b) (S)-[1-(4-Benzyloxy-phenyl)-2-oxo-pyrrolidin-3-yl]-carbamic Acid Tert-Butyl Ester A mixture of 0.35 g (0.81 mmol) of (S)-[1-(4-benzyloxy-phenylcarbamoyl)-3-methylsulfanyl-propyl]-carbamic acid tert-butyl ester and 8.79 g (62.0 mmol) of methyliodide is stirred at RT for 3 d. Thereafter, the methyliodide is evaporated, the intermediate sulfonium salt dissolved in 15 ml of THF and treated with 0.79 ml (0.79 ml) of lithium bis-(trimethylsilyl)amide (1 M solution in THF) at 0° C. After stirring at 0° C. for 2 h, the reaction mixture is evaporated under reduced pressure and the solid residue is directly submitted to chromatography on silica gel using a 2:1 mixture of n-hexane and ethyl acetate as the eluent. There are obtained 0.175 mg (56% of theory) of (S)-[1-(4-benzyloxy-phenyl)-2-oxo-pyrrolidin-3-yl]-carbamic acid tert-butyl ester as a white solid. MS: m/e=383 (M+H)$^+$.

c) (S)-3-Amino-1-(4-benzyloxy-phenyl)-pyrrolidin-2-one Hydrochloride

A solution of 137 mg (0.36 mmol) of (S)-[1-(4-benzyloxy-phenyl)-2-oxo-pyrrolidin-3-yl]-carbamic acid tert-butyl ester in 2 ml of dioxane is treated with 0.3 ml of hydrochloric acid (37%). The solution is warmed to 45° C. for 1 h forming a white suspension. For the working-up, the reaction mixture is evaporated under reduced pressure and the solid residue is triturated with a small volume of methanol. After filtration and drying, 94 mg of (S)-3-amino-1-(4-benzyloxy-phenyl)-pyrrolidin-2-one hydrochloride (82% of theory) are obtained as a white solid. MS: m/e=283 (M+H)$^+$.

d) (S)-N-[1-(4-Benzyloxy-phenyl)-2-oxo-pyrrolidin-3-yl]-acetamide

A solution of 40 mg (0.13 mmol) of (S)-3-amino-1-(4-benzyloxy-phenyl)-pyrrolidin-2-one hydrochloride in 2 ml of dichloromethane is treated with 38 μl (0.28 mmol) of triethylamine and cooled to 0° C. To this solution, 10 μl (0.14 mmol) of acetylchloride are added and stirring at 0° C. is continued for 30 min. For the working-up, the reaction mixture is treated with 2 ml of ammonium hydroxide solution, the organic phase separated, thereafter dried over sodium sulfate and evaporated under reduced pressure. For purification, the material obtained is chromatographed on silica gel using a 95:5 mixture of dichloromethane and methanol as the eluent. There are obtained 31 mg (76% of theory) of (S)-N-[1-(4-enzyloxy-phenyl)-2-oxo-pyrrolidin-3-yl]-acetamide as a white solid. MS: m/e=325 (M+H)$^+$.

EXAMPLE 9

(S)-N-[1-(4-Benzyloxy-phenyl)-2-oxo-pyrrolidin-3-yl]-methanesulfonamide

In an analogous manner to that described in Example 8d), the reaction of (S)-3-amino-1-(4-benzyloxy-phenyl)-pyrrolidin-2-one hydrochloride with methanesulfochloride in the presence of triethylamine yields (S)-N-[1-(4-benzyloxy-phenyl)-2-oxo-pyrrolidin-3-yl]-methanesulfonamide as a white solid. MS: m/e=361 (M+H)$^+$.

EXAMPLE 10

(S)-N-{1-[4-(3-Fluoro-benzyloxy)-phenyl]-2-oxo-pyrrolidin-3-yl}-acetamide a) In an analogous manner to that described in Example 8a) to c), the (S)-3-amino-1-[4-(3-fluoro-benzyloxy)-phenyl]-pyrrolidin-2-one hydrochloride is obtained:

Condensation of (S)-BOC-methionine and 4-(3-fluorobenzyloxy)-phenylamine [Example 3b)] by HBTU yields the (S)-{1-[4-(3-fluoro-benzyloxy)-phenylcarbamoyl]-3-methylsulfanyl-propyl}-carbamic acid tert-butyl ester as a light yellow solid; MS: m/e=449 (M+H)$^+$. The following methylation and cyclisation yields the (S)-{1-[4-(3-fluoro-benzyloxy)-phenyl]-2-oxo-pyrrolidin-3-yl}-carbamic acid tert-butyl ester as a white solid; MS: m/e=401 (M+H)⁺. The cleavage of the BOC-group yields the (S)-3-amino-1-[4-(3-fluoro-benzyloxy)-phenyl]-pyrrolidin-2-one hydrochloride as a white solid; MS: m/e=301 (M+H)⁺.

b) (S)-N-{1-[4-(3-fluoro-benzyloxy)-phenyl]-2-oxo-pyrrolidin-3-yl}-acetamide

In an analogous manner to that described in Example 8d), the acetylation of the (S)-3-amino-1-[4-(3-fluoro-benzyloxy)-phenyl]-pyrrolidin-2-one hydrochloride yields the title compound as a white solid; MS: m/e=343 (M+H)⁺.

EXAMPLE 11

(R)-N-{1-[4-(3-fluoro-benzyloxy)-phenyl]-2-oxo-pyrrolidin-3-yl}-acetamide, (R)-N-{1-[4-(3-fluoro-benzyloxy)-phenyl]-2-oxo-pyrrolidin-3-yl}-methanesulfonamide, (S)-N-{1-[4-(3-fluoro-benzyloxy)-phenyl]-2-oxo-pyrrolidin-3-yl}-methanesulfonamide and (S)-{1-[4-(3-fluoro-benzyloxy)-phenyl]-2-oxo-pyrrolidin-3-yl}-carbamic Acid Methyl ester In an analogous manner to that described in Example 8 d), the acylation of (R)- or (S)-3-amino-1-[4-(3-fluoro-benzyloxy)-phenyl]-pyrrolidin-2-one hydrochloride [the (R)-isomer is obtained in analogy to the (S)-isomer as described in Example 10 a) starting from (R)-BOC-methionine] yield the following compounds:

a) Reaction of the (R)-3-amino-1-[4-(3-fluoro-benzyloxy)-phenyl]-pyrrolidin-2-one hydrochloride with acetylchloride yields the (R)-N-{1-[4-(3-fluoro-benzyloxy)-phenyl]-2-oxo-pyrrolidin-3-yl}-acetamide as a white solid; MS: m/e=343 (M+H)⁺.

b) Reaction of the (R)-3-amino-1-[4-(3-fluoro-benzyloxy)-phenyl]-pyrrolidin-2-one hydrochloride with methanesulfochloride yields the (R)-N-{1-[4-(3-fluoro-benzyloxy)-phenyl]-2-oxo-pyrrolidin-3-yl}-methanesulfonamide as a white solid; MS: m/e=377 (M+H)⁺.

c) Reaction of the (S)-3-amino-1-[4-(3-fluoro-benzyloxy)-phenyl]-pyrrolidin-2-one hydrochloride with methanesulfochloride yields the (S)-N-{1-[4-(3-fluoro-benzyloxy)-phenyl]-2-oxo-pyrrolidin-3-yl}-methanesulfonamide as a white solid; MS: m/e=377 (M+H)⁺.

d) Reaction of the (S)-3-amino-1-[4-(3-fluoro-benzyloxy)-phenyl]-pyrrolidin-2-one hydrochloride with methyl chloroformate yields the (S)-{1-[4-(3-fluoro-benzyloxy)-phenyl]-2-oxo-pyrrolidin-3-yl}-carbamic acid methyl ester as a white solid; MS: m/e=359 (M+H)⁺.

EXAMPLE 12

(R)-N-{1-[4-(3-Fluoro-benzyloxy)-phenyl]-2-oxo-pyrrolidin-3-yl}-formamide

A mixture of 188 mg (18 mmol) of acetic anhydride and 107 mg (23 mmol) of formic acid is prepared at 0° C., thereafter, heated to 60° C. for 2 hours. After cooling to RT, the mixture is diluted with 1 ml of tetrahydrofurane and a solution of 213 mg (7 mmol) of (R)-3-amino-1-[4-(3-fluoro-benzyloxy)-phenyl]-pyrrolidin-2-one in 2 ml of dichloromethane, beforehand prepared from the corresponding hydrochloride by treatment with triethylamine, is added. After the addition a white suspension is formed which is stirred at RT for 1 hour. For the working-up, the reaction mixture is treated with dichloromethane and water, then, the organic layer is separated, dried over sodium sulfate and evaporated. There are obtained 215 mg (92% of theory) of (R)-N-{1-[4-(3-Fluoro-benzyloxy)-phenyl]-2-oxo-pyrrolidin-3-yl}-formamide as a white solid; MS: m/e=329 (M+H)⁺.

EXAMPLE 13

(S)-N-{1-[4-(3-Fluoro-benzyloxy)-phenyl]-2-oxo-pyrrolidin-3-yl}-formamide

In an analogous manner to that described in Example 12, the reaction of (S)-3-amino-1-[4-(3-fluoro-benzyloxy)-phenyl]-pyrrolidin-2-one with a mixture of acetic anhydride and formic acid yields the title compound as a white solid; MS: m/e=329 (M+H)⁺.

EXAMPLE 14

(R)-{1-[4-(3-Fluoro-benzyloxy)-phenyl]-2-oxo-pyrrolidin-3-yl}-urea

A solution of 250 mg (0.7 mmol) of (R)-3-amino-1-[4-(3-fluoro-benzyloxy)-phenyl]-pyrrolidin-2-one hydrochloride and 294 mg (2.2 mmol) of N-ethyl-diisopropylamine in 2 ml of N,N-dimethylformamide is cooled to 0° C. and treated with 267 mg (2.2 mol) of trimethylisocyanate. The reaction mixture is left to warm to RT and stirring is continued for 2 days. For the working-up, the suspension is evaporated under reduced pressure. The crude product is triturated in water, then the recovered solid material triturated a second time in a mixture of ethyl acetate and a saturated solution of sodium hydrogencarbonate. The remaining solid is collected on a filter funnel to give, after drying under high vacuum, 155 mg (61% of theory) of (R)-{1-[4-(3-fluoro-benzyloxy)-phenyl]-2-oxo-pyrrolidin-3-yl}-urea as a white solid; MS: m/e=344 (M+H)⁺.

EXAMPLE 15

(S)-{1-[4-(3-Fluoro-benzyloxy)-phenyl]-2-oxo-pyrrolidin-3-yl}-urea

In an analogous manner to that described in Example 14, the reaction of (S)-3-amino-1-[4-(3-fluoro-benzyloxy)-phenyl]-pyrrolidin-2-one trimethylisocyanate yields the title compound as a white solid; MS: m/e=344 (M+H)⁺.

EXAMPLE 16

(S)-N-{1-(S)-[4-(4-Fluoro-benzyloxy)-phenyl]-2-oxo-pyrrolidin-3-yl}-acetamide a) (S)-[1-(4-Hydroxy-phenyl)-2-oxo-pyrrolidin-3-yl]-carbamic Acid Tert-Butyl Ester In an analogous manner to that described in Example 2b), the hydrogenolysis of the (S)-[1-(4-benzyloxy-phenyl)-2-oxo-pyrrolidin-3-yl]-carbamic acid tert-butyl ester [Example 8 b)] using palladium on carbon as the catalyst yields the title compound as a white solid in quantitative yield; MS: m/e=291 (M−H)⁺.

b) (S)-{1-[4-(4-Fluoro-benzyloxy)-phenyl]-2-oxo-pyrrolidin-3-yl}-carbamic Acid Tert-Butyl Ester In an analogous manner to that described in Example 2c), the alkylation of the (S)-[1-(4-hydroxy-phenyl)-2-oxo-pyrrolidin-3-yl]-carbamic acid tert-butyl ester with 4-fluorobenzylbromide in presence of potassium carbonate yields the title compound as a white solid; MS: m/e=401 (M+H)$^+$.

c) (S)-3-Amino-1-[4-(4-fluoro-benzyloxy)-phenyl]-pyrrolidin-2-one Hydrochloride

In an analogous manner to that described in Example 8c), the cleavage of the BOC-group of the (S)-{1-[4-(4-fluoro-benzyloxy)-phenyl]-2-oxo-pyrrolidin-3-yl}-carbamic acid tert-butyl ester yields the title compound as a white solid; MS: m/e=301 (M+H)$^+$.

d) (S)-N-{1-[4-(4-fluoro-benzyloxy)-phenyl]-2-oxo-pyrrolidin-3-yl}-acetamide

In an analogous manner to that described in Example 8 d), the acetylation of the (S)-3-amino-1-[4-(4-fluoro-benzyloxy)-phenyl]-pyrrolidin-2-one hydrochloride yields the title compound as a white solid; MS: m/e=343 (M+H)$^+$.

EXAMPLE 17

(S)—N-{1-(S)-[4-(2,6-Difluoro-benzyloxy)-phenyl]-2-oxo-pyrrolidin-3-yl}-acetamide a) (S)-{1-[4-(2,6-Difluoro-benzyloxy)-phenyl]-2-oxo-pyrrolidin-3-yl}-carbamic Acid Tert-Butyl Ester In an analogous manner to that described in Example 2c), the alkylation of the (S)-[1-(4-hydroxy-phenyl)-2-oxo-pyrrolidin-3-yl]-carbamic acid tert-butyl ester [Example 16 a)] with 2,6-difluorobenzylbromide in presence of potassium carbonate yields the title compound as a white solid; MS: m/e=419 (M+H)$^+$.

b) (S)-3-Amino-1-[4-(2,6-difluoro-benzyloxy)-phenyl]-pyrrolidin-2-one Hydrochloride In an analogous manner to that described in Example 8c), the cleavage of the BOC-group of the (S)-{1-[4-(2,6-difluoro-benzyloxy)-phenyl]-2-oxo-pyrrolidin-3-yl}-carbamic acid tert-butyl ester yields the title compound as a white solid.

c) (S)-N-{1-[4-(2,6-difluoro-benzyloxy)-phenyl]-2-oxo-pyrrolidin-3-yl}-acetamide In an analogous manner to that described in Example 8 d), the acetylation of the (S)-3-amino-1-[4-(2,6-difluoro-benzyloxy)-phenyl]-pyrrolidin-2-one hydrochloride yields the title compound as a white solid; MS: m/e=361 (M+H)$^+$.

EXAMPLE 18

(S)-N-{1-[4-(3,4-Difluoro-benzyloxy)-phenyl]-2-oxo-pyrrolidin-3-yl}-acetamide a) (S)-{1-[4-(3,4-Difluoro-benzyloxy)-phenyl]-2-oxo-pyrrolidin-3-yl}-carbamic Acid Tert-Butyl Ester In an analogous manner to that described in Example 2c), the alkylation of the (S)-[1-(4-hydroxy-phenyl)-2-oxo-pyrrolidin-3-yl]-carbamic acid tert-butyl ester [Example 16 a)] with 3,4-difluorobenzylbromide in presence of potassium carbonate yields the title compound as a white solid; MS: m/e=419 (M+H)$^+$.

b) (S)-3-Amino-1-[4-(3,4-difluoro-benzyloxy)-phenyl]-pyrrolidin-2-one Hydrochloride In an analogous manner to that described in Example 8c), the cleavage of the BOC-group of the (S)-{1-[4-(3,4-difluoro-benzyloxy)-phenyl]-2-oxo-pyrrolidin-3-yl}-carbamic acid tert-butyl ester yields the title compound as a white solid; MS: m/e=319 (M+H)$^+$.

c) (S)-N-{1-[4-(3,4-difluoro-benzyloxy)-phenyl]-2-oxo-pyrrolidin-3-yl}-acetamide In an analogous manner to that described in Example 8 d), the acetylation of the (S)-3-amino-1-[4-(3,4-difluoro-benzyloxy)-phenyl]-pyrrolidin-2-one hydrochloride yields the title compound as a white solid; MS: m/e=361 (M+H)$^+$.

The following Examples A to D are prophetic.

EXAMPLE A

Tablets

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

Injection Solution

An injection solution may have the following composition and is manufactured in usual manner:

| | |
|---|---|
| Active substance | 1.0 mg |
| 1 N HCl | 20.0 μl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

The invention claimed is:

1. A compound of the formula I

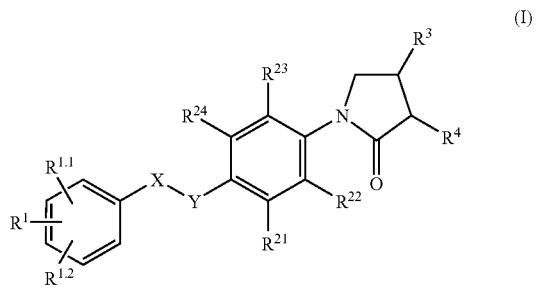

wherein

X—Y is —CH$_2$—CH$_2$—, —CH=CH— or —CH$_2$—O—;

$R^1$, $R^{1.1}$ and $R^{1.2}$ independently from each other are selected from the group consisting of hydrogen, halogen, cyano, (C$_1$–C$_6$)-alkyl, halogen-(C$_1$–C$_6$)-alkyl, (C$_1$–C$_6$)-alkoxy or halogen-(C$_1$–C$_6$)-alkoxy;

$R^{21}$, $R^{22}$ and $R^{23}$ independently from each other are selected from the group consisting of hydrogen and halogen;

$R^{24}$ is hydrogen, halogen or methyl;

$R^3$ is hydrogen;

$R^4$ is —CONHR$^5$, —CN or —NHR$^6$;

$R^5$ is hydrogen or (C$_1$–C$_3$)-alkyl; and $R^6$ is —CO—H, —CO—(C$_1$–C$_6$)-alkyl, —CO-halogen-(C$_1$–C$_3$)-alkyl, —CO—O—(C$_1$–C$_3$)-alkyl, —CO—NH$_2$ or —SO$_2$—(C$_1$–C$_6$)-alkyl;

or an individual isomer or racemic or non-racemic mixture thereof.

2. A compound according to claim 1 wherein —X—Y— is —CH$_2$—O—.

3. A compound according to claim 2 wherein $R^1$, $R^{1.1}$, and $R^{1.2}$ independently are hydrogen, halogen, methyl, halogenmethyl, cyano, methoxy or halogenmethoxy.

4. A compound according to claim 3 wherein $R^{21}$, $R^{22}$, $R^{23}$, and $R^{24}$ are hydrogen.

5. A compound according to claim 4 wherein $R^4$ is CN.

6. A compound according to claim 4 wherein $R^4$ is CONHR$^5$ and $R^5$ is hydrogen or (C$_1$–C$_3$)-alkyl.

7. A compound according to claim 4 wherein $R^4$ is NHR$^6$ and $R^6$ is —CO—H, —CO—(C$_1$–C$_6$)-alkyl, —CO-halogen-(C$_1$–C$_3$)-alkyl, —CO—O—(C$_1$–C$_3$)-alkyl, —CO—NH$_2$ or —SO$_2$—(C$_1$–C$_6$)-alkyl.

8. A compound according to claim 2 wherein $R^{1.2}$ is hydrogen and $R^1$ and $R^{1.1}$ independently are each hydrogen, halogen, cyano, (C$_1$–C$_6$)-alkyl, halogen-(C$_1$–C$_6$)-alkyl, (C$_1$–C$_6$)-alkoxy or halogen-(C$_1$–C$_6$)-alkoxy.

9. A compound according to claim 8 wherein $R^{21}$, $R^{22}$, $R^{23}$, and $R^{24}$ are hydrogen.

10. A compound according to claim 9 wherein $R^4$ is CN.

11. A compound according to claim 9 wherein $R^4$ is CONHR$^5$ and $R^5$ is hydrogen or (C$_1$–C$_3$)-alkyl.

12. A compound according to claim 9 wherein $R^4$ is NHR$^6$ and $R^6$ is —CO—H, —CO—(C$_1$–C$_6$)-alkyl, —CO-halogen-(C$_1$–C$_3$)-alkyl, —CO—O—(C$_1$–C$_3$)-alkyl, —CO—NH$_2$ or —SO$_2$—(C$_1$–C$_6$)-alkyl.

13. A compound according to claim 2 wherein $R^{1.1}$ and $R^{1.2}$ are hydrogen and $R^1$ is halogen, cyano, (C$_1$–C$_6$)-alkyl, halogen-(C$_1$–C$_6$)-alkyl, (C$_1$–C$_6$)-alkoxy or halogen-(C$_1$–C$_6$)-alkoxy.

14. A compound according to claim 13 wherein $R^{21}$, $R^{22}$, $R^{23}$, and $R^{24}$ are hydrogen.

15. A compound according to claim 14 wherein $R^4$ is CN.

16. A compound according to claim 14 wherein $R^4$ is CONHR$^5$ and $R^5$ is hydrogen or (C$_1$–C$_3$)-alkyl.

17. A compound according to claim 14 wherein $R^4$ is NHR$^6$ and $R^6$ is —CO—H, —CO—(C$_1$–C$_6$)-alkyl, —CO-halogen-(C$_1$–C$_3$)-alkyl, —CO—O—(C$_1$–C$_3$)-alkyl, —CO—NH$_2$ or —SO$_2$—(C$_1$–C$_6$)-alkyl.

18. A compound according to claim 17 wherein $R^1$ is halogen and $R^6$ is —CO—(C$_1$–C$_6$)-alkyl.

19. A compound according to claim 18 wherein $R^6$ is COCH$_3$.

20. A compound according to claim 2 wherein $R^1$, $R^{1.1}$, $R^{1.2}$, $R^{21}$, $R^{22}$, $R^{23}$, and $R^{24}$ are hydrogen.

21. A compound according to claim 20 wherein $R^4$ is CN.

22. A compound according to claim 20 wherein $R^4$ is CONHR$^5$ and $R^5$ is hydrogen or (C$_1$–C$_3$)-alkyl.

23. A compound according to claim 20 wherein $R^4$ is NHR$^6$ and $R^6$ is —CO—H, —CO—(C$_1$–C$_6$)-alkyl, —CO-halogen-(C$_1$–C$_3$)-alkyl, —CO—O—(C$_1$–C$_3$)-alkyl, —CO—NH$_2$ or —SO$_2$—(C$_1$–C$_6$)-alkyl.

24. A compound according to claim 1 wherein $R^{21}$, $R^{22}$, and $R^{23}$ are hydrogen.

25. A compound according to claim 1 wherein $R^{24}$ is hydrogen.

26. A compound according to claim 1 wherein $R^4$ is —CONHR$^5$, wherein $R^5$ is hydrogen or (C$_1$–C$_3$)-alkyl.

27. A compound according to claim 26 wherein $R^5$ is hydrogen or methyl.

28. A compound according to claim 1 wherein $R^4$ is —CN.

29. A compound according to claim 1 wherein $R^4$ is —NHR$^6$, wherein $R^6$ is —CO—H, —CO—(C$_1$–C$_6$)-alkyl, —CO-halogen-(C$_1$–C$_3$)-alkyl, —CO—O—(C$_1$–C$_3$)-alkyl, —CO—NH$_2$ or —SO$_2$—(C$_1$–C$_6$)-alkyl.

30. A compound according to claim 29 wherein $R^6$ is —CO—H, —CO—CH$_3$, —CO—O—CH$_3$, —CO—NH$_2$ or —SO$_2$—CH$_3$.

31. A compound according to claim 1 wherein the compound has (S)-configuration.

32. A compound according to claim 1 wherein the compound has (R)-configuration.

33. A compound according to claim 1 wherein $R^1$, $R^{1.1}$ and $R^{1.2}$ independently from each other are selected from the group consisting of hydrogen, halogen, methyl, halogenmethyl, cyano, methoxy or halogen-methoxy.

34. A compound according to claim 1 wherein $R^{1.2}$ is hydrogen and $R^1$ and $R^{1.1}$ independently from each other are selected from the group consisting of hydrogen, halogen, cyano, $(C_1–C_6)$-alkyl, halogen-$(C_1–C_6)$-alkyl, $(C_1–C_6)$-alkoxy or halogen-$(C_1–C_6)$-alkoxy.

35. A compound according to claim 34 wherein $R^{1.1}$ is hydrogen.

36. A compound according to claim 35 wherein $R^1$ is halogen, methyl, halogenmethyl, cyano, methoxy or halogen-methoxy.

37. A compound according to claim 36 wherein $R^1$ is halogen.

38. A compound according to claim 37 wherein $R^1$ is fluoro.

39. A compound according to claim 38, wherein $R^1$ is 3-fluoro or 4-fluoro.

40. A compound according to claim 37 wherein $R^1$ is chloro.

41. A compound according to claim 40 wherein $R^1$ is 3-chloro.

42. A compound according to claim 36 wherein $R^1$ is halogenmethyl.

43. A compound according to claim 42 wherein $R^1$ is 3-trifluoromethyl or 4-trifluoromethyl.

44. A compound according to claim 36 wherein $R^1$ is CN.

45. A compound according to claim 36 wherein $R^1$ is methoxy.

46. A compound according to claim 45 wherein $R^1$ is 2-methoxy, 3-methoxy, or 4-methoxy.

47. A compound according to claim 36 wherein $R^1$ is halogenmethoxy.

48. A compound according to claim 47 wherein $R^1$ is 3-trifluoromethoxy.

49. A compound according to claim 34 wherein $R^{1.2}$ is hydrogen and $R^1$ and $R^{1.1}$ independently are each halogen or $(C_1–C_6)$-alkyl.

50. A compound according to claim 49 wherein $R^{1.2}$ is hydrogen, $R^{1.1}$ is halogen, and $R^1$ is halogen or $(C_1–C_6)$-alkyl.

51. A compound according to claim 1 wherein $R^1$, $R^{1.1}$, and $R^{1.2}$ are halogen.

52. A compound according to claim 51 wherein $R^1$, $R^{1.1}$, and $R^{1.2}$ are fluoro.

53. A compound according to claim 52 wherein $R^1$, $R^{1.1}$, and $R^{1.2}$ are 2,4,6-trifluoro, 2,4,5-trifluoro, 2,3,6-trifluoro, 2,3,4-trifluoro, or 3,4,5-trifluoro.

54. A compound according to claim 1 wherein $R^1$, $R^{1.1}$, and $R^{1.2}$ are hydrogen.

55. A compound of the formula I*

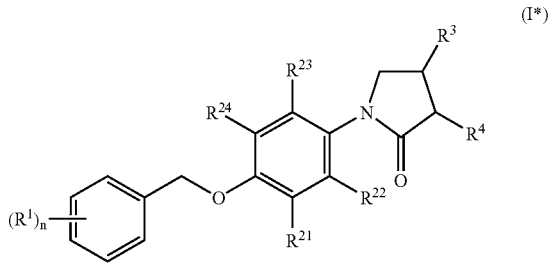

(I*)

wherein
$R^1$ is halogen, halogen-$(C_1–C_6)$-alkyl, cyano, $(C_1–C_6)$-alkoxy or halogen-$(C_1–C_6)$-alkoxy;
$R^{21}$, $R^{22}$, $R^{23}$ and $R^{24}$ independently from each other are selected from the group consisting of hydrogen and halogen;
$R^3$ is hydrogen;
$R^4$ is —$CONHR^5$, —CN or —$NHR^6$;
$R^5$ is hydrogen or $C_1–C_3$-alkyl;
$R^6$ is —CO—$(C_1–C_6)$-alkyl or —$SO_2$—$(C_1–C_6)$-alkyl; and
n is 0, 1, 2 or 3;
or an individual isomer or racemic or non-racemic mixture thereof.

56. A compound according to claim 55 wherein $R^3$ is hydrogen, $R^4$ is CN, or $CONHR^5$.

57. A compound according to claim 55 wherein $R^4$ is $CONHR^5$ and $R^5$ is hydrogen or $(C_1–C_3)$-alkyl.

58. A compound according to claim 55 wherein $R^4$ is CN.

59. A compound according to claim 55 wherein $R^4$ is $NHR^6$ and $R^6$ is —CO—$(C_1–C_6)$-alkyl or —$SO_2$—$(C_1–C_6)$-alkyl.

60. A compound according to claim 55 wherein $R^3$ is hydrogen, $R^4$ is $NHR^6$ and $R^6$ is —CO—$(C_1–C_6)$-alkyl or —$SO_2$—$(C_1–C_6)$-alkyl.

61. A compound according to claim 55 wherein $R^1$ is halogen or halogen-$(C_1–C_6)$-alkyl.

62. A compound according to claim 61 wherein $R^1$ is fluoro, chloro, or trifluoromethyl.

63. A compound according to claim 55 wherein n is 1 or 2.

64. A compound selected from the group consisting of
(RS)-1-(4-benzyloxy-phenyl)-2-oxo-pyrrolidine-3-carbonitrile,
(RS)-1-[4-(3-fluoro-benzyloxy)-phenyl]-2-oxo-pyrrolidine-3-carboxylic acid methylamide,
(RS)-1-[4-(3-fluoro-benzyloxy)-phenyl]-2-oxo-pyrrolidine-3-carboxylic acid amide,
(RS)-1-[4-(4-fluoro-benzyloxy)-phenyl]-2-oxo-pyrrolidine-3-carboxylic acid amide,
(RS)-1-[4-(4-fluoro-benzyloxy)-phenyl]-2-oxo-pyrrolidine-3-carboxylic acid methylamide,
(RS)-2-oxo-1-[4-(4-trifluoromethyl-benzyloxy)-phenyl]-pyrrolidine-3-carboxylic acid amide, and
(RS)-2-oxo-1-[4-(4-trifluoromethyl-benzyloxy)-phenyl]-pyrrolidine-3-carboxylic acid methylamide.

65. A compound selected from the group consisting of
(S)-N-[1-(4-benzyloxy-phenyl)-2-oxo-pyrrolidin-3-yl]-acetamide,
(S)-N-[1-(4-benzyloxy-phenyl)-2-oxo-pyrrolidin-3-yl]-methanesulfonamide,
(S)-N-{1-[4-(3-fluoro-benzyloxy)-phenyl]-2-oxo-pyrrolidin-3-yl}-acetamide,
(R)-N-{1-[4-(3-fluoro-benzyloxy)-phenyl]-2-oxo-pyrrolidin-3-yl}-acetamide,
(R)-N-{1-[4-(3-fluoro-benzyloxy)-phenyl]-2-oxo-pyrrolidin-3-yl}-methanesulfonamide,
(S)-N-{1-[4-(3-fluoro-benzyloxy)-phenyl]-2-oxo-pyrrolidin-3-yl}-methanesulfonamide, and
(S)-{1-[4-(3-fluoro-benzyloxy)-phenyl]-2-oxo-pyrrolidin-3-yl}-carbamic acid methyl ester.

66. A compound selected from the group consisting of
(R)-N-{1-[4-(3-fluoro-benzyloxy)-phenyl]-2-oxo-pyrrolidin-3-yl}-formamide,
(S)-N-{1-[4-(3-fluoro-benzyloxy)-phenyl]-2-oxo-pyrrolidin-3-yl}-formamide, (R)-{1-[4-(3-fluoro-benzyloxy)-phenyl]-2-oxo-pyrrolidin-3-yl}-urea,
(S)-{1-[4-(3-fluoro-benzyloxy)-phenyl]-2-oxo-pyrrolidin-3-yl}-urea,
(S)-N-{1-(S)-[4-(4-fluoro-benzyloxy)-phenyl]-2-oxo-pyrrolidin-3-yl}-acetamide,
(S)-N-{1-(S)-[4-(2,6-difluoro-benzyloxy)-phenyl]-2-oxo-pyrrolidin-3-yl}-acetamide, and
(S)-N-{1-[4-(3,4-difluoro-benzyloxy)-phenyl]-2-oxo-pyrrolidin-3-yl}-acetamide.

67. A composition comprising a compound of formula I

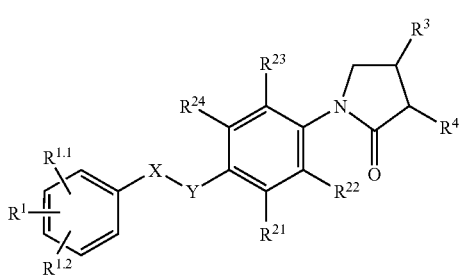

(I)

wherein
X—Y is —$CH_2$—$CH_2$—, —CH=CH— or —$CH_2$—O—;
$R^1$, $R^{1.1}$ and $R^{1.2}$ independently from each other are selected from the group consisting of hydrogen, halogen, cyano, ($C_1$–$C_6$)-alkyl, halogen-($C_1$–$C_6$)-alkyl, ($C_1$–$C_6$)-alkoxy or halogen-($C_1$–$C_6$)-alkoxy;
$R^{21}$, $R^{22}$ and $R^{23}$ independently from each other are selected from the group consisting of hydrogen and halogen;
$R^{24}$ is hydrogen, halogen or methyl;
$R^3$ is hydrogen;
$R^4$ is —$CONHR^5$, —CN or —$NHR^6$;
$R^5$ is hydrogen or ($C_1$–$C_3$)-alkyl; and
$R^6$ is —CO—H, —CO—($C_1$–$C_6$)-alkyl, —CO-halogen-($C_1$–$C_3$)-alkyl, —CO—O—($C_1$–$C_3$)-alkyl, —CO—$NH_2$ or —$SO_2$—($C_1$–$C_6$)-alkyl;
or an individual isomer or racemic or non-racemic mixture thereof, and a pharmaceutically acceptable carrier.

68. A composition comprising a compound of formula I*

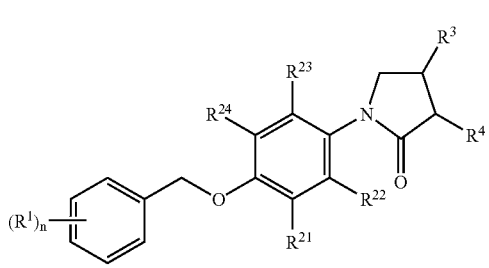

(I*)

wherein
$R^1$ is halogen, halogen-($C_1$–$C_6$)-alkyl, cyano, ($C_1$–$C_6$)-alkoxy or halogen-($C_1$–$C_6$)-alkoxy;
$R^{21}$, $R^{22}$, $R^{23}$ and $R^{24}$ independently from each other are selected from the group consisting of hydrogen and halogen;
$R^3$ is hydrogen;
$R^4$ is —$CONHR^5$, —CN or —$NHR^6$;
$R^5$ is hydrogen or $C_1$–$C_3$-alkyl;
$R^6$ is —CO—($C_1$–$C_6$)-alkyl or —$SO_2$—($C_1$–$C_6$)-alkyl; and
n is 0, 1, 2 or 3;
or an individual isomer or racemic or non-racemic mixture thereof, and a pharmaceutically acceptable carrier.

69. A process for the preparation of compounds of formula I according to claim 1 wherein $R^4$ is $CONHR^5$ comprising reacting a compound of formula II

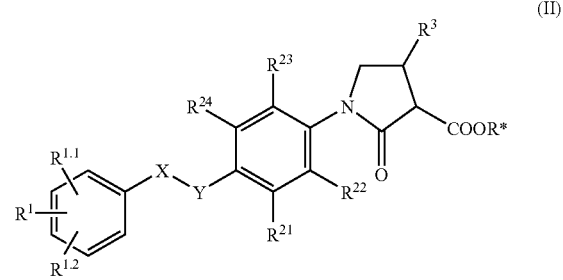

(II)

wherein $R^1$, $R^{1.1}$, $R^{1.2}$, $R^{21}$, $R^{22}$, $R^{23}$, $R^{24}$, $R^3$, X and Y have the meanings as defined in claim 1 and R* is hydrogen or ($C_1$–$C_6$)-alkyl,
with an amine of formula $H_2N$—$R^5$, wherein $R^5$ has the meaning in claim 1.

70. A process for the preparation of compounds of formula I according to claim 1 wherein $R^4$ is CN comprising reacting a compound of formula III

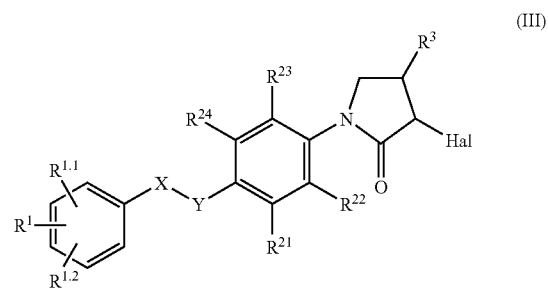

(III)

wherein $R^1$, $R^{1.1}$, $R^{1.2}$, $R^{21}$, $R^{22}$, $R^{23}$, $R^{24}$, $R^3$, X and Y have the meanings as defined in claim 1 and Hal is halogen,
with a cyanide salt.

71. A process for the preparation of compounds of formula I according to claim 1 wherein $R^4$ is $NHR^6$ comprising reacting a compound of formula IV

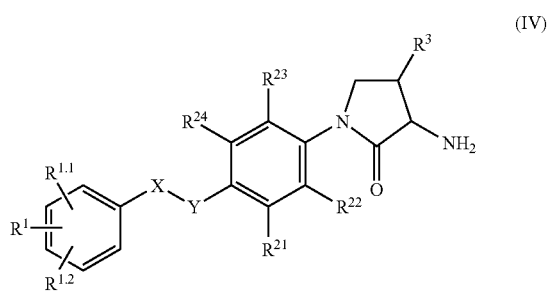

(IV)

wherein $R^1$, $R^{1.1}$, $R^{1.2}$, $R^{21}$, $R^{22}$, $R^{23}$, $R^{24}$, $R^3$, X and Y have the meanings as defined in claim 1, with an acyl donating agent of formula Z-CO—H, Z-CO—$(C_1$–$C_6)$-alkyl, Z-CO-halogen-$(C_1$–$C_3)$-alkyl, Z-CO—O—$(C_1$–$C_3)$-alkyl, or Z-SO$_2$—$(C_1$–$C_3)$-alkyl wherein Z is an activating group.

72. A method for the treatment of Alzheimer's disease comprising administering to an individual a therapeutically effective amount of a compound of claim 1.

73. A method for the treatment of senile dementia comprising administering to an individual a therapeutically effective amount of a compound of claim 1.

* * * * *

UNITED STATES PATENT AND TRADEMARK OFFICE
CERTIFICATE OF CORRECTION

PATENT NO. : 7,235,581 B2  Page 1 of 1
APPLICATION NO. : 10/666594
DATED : June 26, 2007
INVENTOR(S) : Jolidon et al.

It is certified that error appears in the above-identified patent and that said Letters Patent is hereby corrected as shown below:

On TITLE PAGE: Item (73)

-The Assignee data reads "Assignee: Hoffman-La Roche Inc., Nutley, NJ (US)". The Assignee data should read -- Hoffmann-La Roche Inc., Nutley, NJ (US) --.

Signed and Sealed this

Twenty-first Day of August, 2007

JON W. DUDAS
*Director of the United States Patent and Trademark Office*